United States Patent [19]

Yukimatsu et al.

[11] Patent Number: 4,740,365

[45] Date of Patent: Apr. 26, 1988

[54] SUSTAINED-RELEASE PREPARATION APPLICABLE TO MUCOUS MEMBRANE IN ORAL CAVITY

[75] Inventors: Keiji Yukimatsu; Munetaka Kakumoto; Yoshihisa Yasuda; Junko Tsujimoto, all of Otsu; Masae Sogabe, Uji, all of Japan

[73] Assignee: Toyo Boseki Kabushiki Kaisha, Osaka, Japan

[21] Appl. No.: 720,461

[22] Filed: Apr. 5, 1985

[30] Foreign Application Priority Data

Apr. 9, 1984 [JP] Japan .................................. 59-71364
May 23, 1984 [JP] Japan ................................ 59-105596

[51] Int. Cl.$^4$ .......................... A61K 9/20; A61K 9/24
[52] U.S. Cl. ..................................................... 424/435
[58] Field of Search ..................................... 424/19–22, 424/78, 80, 435

[56] References Cited

U.S. PATENT DOCUMENTS

| | | | |
|---|---|---|---|
| 4,250,163 | 2/1981 | Nagai et al. | 424/19 |
| 4,292,299 | 9/1981 | Suzuki et al. | 424/16 |
| 4,343,789 | 8/1982 | Kawata et al. | 424/19 |
| 4,404,183 | 9/1983 | Kawata et al. | 424/19 |
| 4,412,986 | 11/1983 | Kawata et al. | 424/80 |
| 4,562,069 | 12/1985 | Hegasy et al. | 424/19 |
| 4,572,832 | 2/1986 | Kigasawa et al. | 424/19 |
| 4,607,041 | 8/1986 | Baxter et al. | 514/356 |
| 4,615,697 | 10/1986 | Robinson | 424/19 |
| 4,617,306 | 10/1986 | Welzel et al. | 514/356 |

Primary Examiner—Shep K. Rose

[57] ABSTRACT

A sustained-release preparation applicable to mucous membrane in oral cavity which comprises an active ingredient and a mixture of a polymer component (A) comprising one or more polymers selected from polyvinylpyrrolidone, polyvinyl alcohol, polyethylene glycol, alginic acid or a salt thereof, and an alternating copolymer of maleic anhydride and methyl vinyl ether and a polymer component (B) comprising one or more polymers selected from polyacrylic acid and a salt thereof, said polymer component (A) and polymer component (B) being contained in a ratio of 95:5 to 5:95 by weight, and optionally in admixture with conventional carrier and additives. Said preparation may be formed in the form of a two-layer preparation with a layer comprising an active ingredient and one or more polymers selected from polyvinylpyrrolidone, polyvinyl alcohol, polyethylene glycol, alginic acid or a salt thereof, and an alternating copolymer of maleic anhydride and methyl vinyl ether and optionally in admixture with conventional carrier and additives. The preparation can easily be adhered to mucous membrane within oral cavity and maintained for a long period of time and the medicament (e.g. nifedipine) contained therein is released into saliva continuously to exhibit the activity effectively.

8 Claims, 16 Drawing Sheets

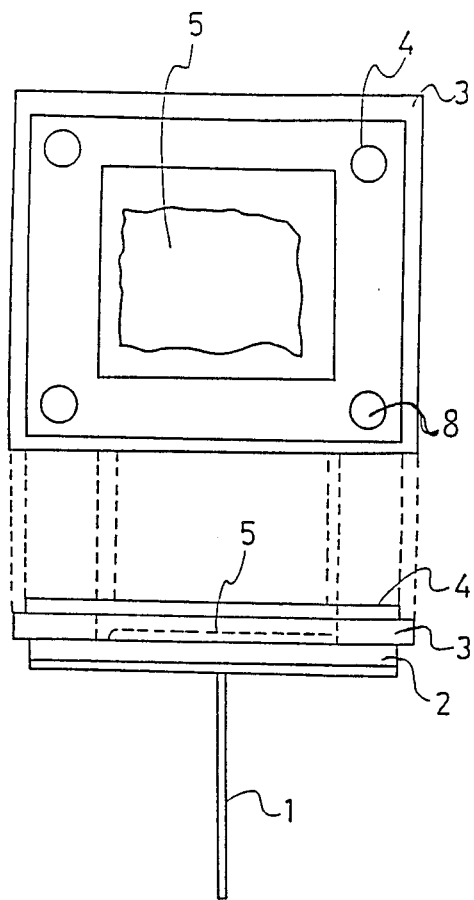
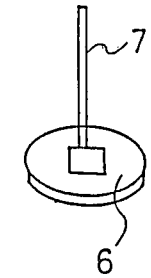
FIG. 7
FIG. 8

SUSTAINED-RELEASE PREPARATION APPLICABLE TO MUCOUS MEMBRANE IN ORAL CAVITY

The present invention relates to a sustained-release preparation applicable to mucous membrane in the oral cavity. More particularly, it relates to an improved sustained-release preparation applicable to mucous membrane in the oral cavity which can easily be adhered to mucous membrane within the oral cavity and maintained for a long period of time and the medicament (e.g. nifedipine) contained therein is released into saliva continuously (not at once) to exhibit the activity effectively.

PRIOR ART

Study of sustained-release preparations has mainly been done on preparations for oral administration. However, these preparations for oral administrations have some drawbacks. For instance, it is difficult to keep the medicament at the desired location so that it can be absorbed; it is easily metabolized in the liver; and it is easily decomposed in stomach. Accordingly, it has been required to develop another sustained-release preparation which can be applied to other organs or tissues in the body.

Besides, there are also well known some preparations which are applicable to the oral cavity, such as buccals, troches, sublingual tablets, and oral ointments. However, these known buccals, troches and sublingual tablets give disadvantageously abnormal feeling to patients when applied in the oral cavity, and hence, the patients occasionally wish to crunch or swallow them, and hence, it is difficult to keep these preparations within the oral cavity. The oral ointments are not crunched or swallowed, but it is difficult to control the dose.

In order to eliminate the above-mentioned drawbacks of the oral preparations, it is proposed to provide a new type of a preparation which can be adhered to the mucous membrane in the oral cavity (cf. Japanese Patent Publication No. 38168/1979). This literature discloses a preparation wherein a medicament is contained in a mixture of sodium polyacrylate and a carrier, but this preparation is easily peeled off from the mucous membrane because of insufficient adhesion and is inferior in the release sustaining, and hence, it is not suitable as a sustained-release preparation. There is also disclosed in Japanese Patent Publication No. 7605/1983 a preparation applicable to mucous membrane in the oral cavity which comprises a combination of hydroxypropyl cellulose and a polyacrylic acid or a pharamceutically acceptable salt thereof. This preparation has an improved adhesion and release sustaining properties in comparison with the above preparation, but is still insufficient in the adhesion.

OBJECT OF THE INVENTION

In view of the above-mentioned drawbacks of the known preparations, the present inventors have intensively investigated a new type of preparation applicable to mucous membrane in the oral cavity which can easily be adhered to mucous membrane in the oral cavity and is not peeled off even in usual action such as eating, drinking or speaking and can be maintained within the oral cavity for a long period of time without bad feeling to release the active ingredient into saliva continuously. As a result, it has been found that the desired preparation can be obtained by incorporating a medicament into a mixture of a specific polymer component with other specific polymer component, which is formed into a shape suitable for applying to mucous membrane and is optionally formed into two-layer preparation by combining a layer comprising a medicament and a layer comprising a specific polymer component.

An object of the present invention is to provide a sustained-release preparation applicable to mucous membrane in the oral cavity comprising an active ingredient and two specific polymer components which can easily be adhered to mucous membrane and release the active ingredient into saliva continuously for a long period of time. Another object of the invention is to provide a sustained-release preparation in the form of a two-layer preparation. These objects and advantages of the present invention will be apparent to persons skilled in the art from the following description.

DETAILED DESCRIPTION OF THE INVENTION

The sustained-release preparation of the present invention comprises an active ingredient and a mixture of a polymer component (A) comprising one or more polymers selected from polyvinylpyrrolidone, polyvinyl alcohol, polyethylene glycol, alginic acid or a pharmaceutically acceptable salt thereof, and an alternating copolymer of maleic anhydride and methyl vinyl ether and a polymer component (B) comprising one or more polymers selected from polyacrylic acid and a pharmaceutically acceptable salt thereof, said polymer component (A) and polymer component (B) being contained in a ratio of 95:5 to 5:95 by weight, and optionally in admixture with conventional carrier and additives.

The polymer component (A) comprises one or more polymers selected from polyvinylpyrrolidone, polyvinyl alcohol, polyethylene glycol, and an alternating copolymer of maleic anhydride and methyl vinyl ether. The polymers may be a copolymerized with other one or more monomers which do not have undesirable effect on the physio-chemical properties of the polymers. When the polymers are copolymerized with not more than 30% by mole of the other monomer(s), the physio-chemical properties of the polymers are not affected, and hence, such copolymers can be used in the present invention.

The pharmaceutically acceptable salts includes alkali metal salts (e.g. sodium salt, or potassium salt), alkaline earth metal salts (e.g. calcium salt), and ammonium salt.

The polymer component (B) comprises one or more polymers selected from polyacrylic acid and a pharmaceutically acceptable salt thereof. The polymers include homopolymers, copolymers of acrylic acid and one or more other monomers, and crosslinked polymers which are crosslinked with an appropriate crosslinking agent. In the case of copolymers with other monomers, in order to prevent any undesirable deterioration of the physio-chemical properties of the homopolymers, the other monomers are used in an amount of not more than 30% by mole. Suitable examples of the polymers which are commercially available are Carbopol 934 ®, Carbopol 940 ®, Carbopol 941 ®.

The desired sustained-release of the active ingredient can be exhibited by using the combination of the polymer component (A) and the polymer component (B). The ratio of the polymer component (A) and the polymer component (B) may be optional, but is preferably in the range of 95:5 to 5:95 by weight. When the polymer component (A) is incorporated in an amount in excess of the above ratio, the desired release sustaining properties is infrequently obtainable, and on the other hand, when the polymer component (B) is incorporated in an amount in excess of the above ratio, the preparation shows disadvantageously too high swell characteristics and hence, such a preparation gives bad feeling when applied to the patients.

The sustained-release preparation applicable to mucous membrane in the oral cavity can be prepared by mixing well the above polymer component (A), polymer component (B) and a medicament (an active ingredient) and optionally one or more additives such as lubricants, binding agents, excipients, flavours, seasonings in order to improve the appearance, flavor and taste, and forming the mixture into a suitable shape with a punch, die, or press, or granulating and then press-forming the granules into a suitable shape, or alternatively dissolving the mixture in a suitable solvent and flowing the solution on a plane vessel, drying to form into a film-like shape.

The sustained-release preparation may be formed into a two layer preparation by combining a layer of the above preparation comprising a medicament and a mixture of a polymer component (A) and a polymer component (B) with a layer comprising a medicament and a specific polymer component. That is, other embodiment of the sustained-release preparation applicable to mucous membrane in oral cavity of the present invention comprises a layer (I) comprising an active ingredient (a medicament) and one or more polymers selected from polyvinylpyrrolidone, polyvinyl alcohol, polyethylene glycol, alginic acid or a pharmaceutically acceptable salt thereof, and an alternating copolymer of maleic anhydride and methyl vinyl ether and optionally in admixture with conventional carrier and additives, said polymers being contained in an amount of not less than 20% by weight based on the whole weight of the layer (I), and a layer (II) comprising an active ingredient (a medicament) and a mixture of a polymer component (A) comprising one or more polymers selected from polyvinylpyrrolidone, polyvinyl alcohol, polyethylene glycol, alginic acid or a pharmaceutically acceptable salt thereof, and an alternating copolymer of maleic anhydride and methyl vinyl ether and a polymer component (B) comprising one or more polymers selected from polyacrylic acid and a pharmaceutically acceptable salt thereof, said polymer component (A) and polymer component (B) being contained in a ratio of 95:5 to 5:95 by weight, and optionally in admixture with conventional carrier and additives.

The layer (I) functions to release the active ingredient in a moderately sustained state. The layer (I) can optionally contain any conventional carriers or additives, but in order to release the active ingredient in a moderately sustained state, the polymer component should be contained in an amount of not less than 20% by weight based on the whole weight of the layer (I). When the polymer component is incorporated in an amount of less than 20% by weight, the active ingredient is released too fast, and hence, even if the layer (I) is combined with the layer (II) which functions to release the active ingredient in a highly sustained state, the sustained-release preparation can not release the active ingredient at a fixed release rate for a long period of time.

The polymers used in the layer (I) may be a copolymerized with one or more other monomers which do not have an undesirable effect on the physio-chemical properties of the polymers, and include also a polymer crosslinked by an appropriate crosslinking agent. When the polymers are copolymerized with not more than 30% by mole of the other monomer(s), the physiochemical properties of the polymers are not affected, and hence, such copolymers can be used in the present invention. The pharmaceutically acceptable salts includes alkali metal salts (e.g. sodium salt, or potassium salt), alkaline earth metal salts (e.g. calcium salt), and ammonium salt.

The layer (II) is the same as the sustained-release preparation as mentioned hereinbefore.

The sustained-release preparation comprising the layer (I) and the layer (II) can be prepared by the steps of forming the layer (I) by mixing well one or more polymer components selected from polyvinylpyrrolidone, polyvinyl alcohol, polyethylene glycol, alginic acid or a pharmaceutically acceptable salt thereof, and an alternating copolymer of maleic anhydride and methyl vinyl ether, a medicament (an active ingredient) and optionally one or more additives such as lubricants, binding agents, excipients, flavours, seasonings in order to improve the appearance, flavor and taste, and forming the mixture into a suitable shape with a punch, die, or press, or granulating and then press-forming the granules into a suitable shape; and then forming the layer (II) on the above layer (I) by laminating a layer of a mixture of the above polymer component (A), polymer component (B) and a medicament (an active ingredient) and optionally one or more additives such as lubricants, binding agents, excipients, flavours, seasonings, followed by pressing.

Alternatively, the sustained-release preparation comprising the layer (I) and the layer (II) can be prepared by preparing separately a solution of the components for each of the layers (I) and (II) in a suitable solvent, flowing each solution onto a plane vessel and drying to form a film-like shape, laminating both layers, and then adhering them with a suitable adhesive, or by wetting them with water or other solvent, followed by pressing, or by heat-pressing with heating, by which there is obtained two-layer preparation (e.g. tablet-shaped preparation).

The active ingredients (medicaments) to be contained in the sustained-release preparation of the present invention include all medicaments useful for oral diseases, diseases of the teeth and also systemic diseases, for example, analgesics and antiinflammatory agents (e.g. indomethacin, ibuprofen), mouth disinfectants (e.g. chlorohexidine hydrochloride, hexylresorcine), enzymes (e.g. lysozyme chloride, dextranase, kallikrein), coronary vasodilators (e.g. nitroglycerin, isosorbide dinitrate, nifedipine), antiasthmatics (e.g. disodium cromoglycate), antibiotics (e.g. penicillins, erythromycin), chemotherapeutics (e.g. sulfathiazole, nitrofurazone), local anesthetics (e.g. benzocaine), cardiotonics (e.g. digitalis, digoxin), antitussives and expectorants (e.g. codeine phosphate, isoproterenol hydrochloride), agents affecting digestive organs [e.g. water-soluble azulene (=sodium azulene sulfonate), vitamin U], antihistamines (e.g. diphenhydramine hydrochloride, chlorpheniramine maleate), antiinflammatory steroids (e.g. prednisolone, triamcinolone), hemostatics, sexual hormones, sedatives, antitumor agents, or the like.

The lubricants used in this invention include, for example, talc, stearic acid and salts thereof, waxes, etc.; the binding agents include, for example, starches, dextrin, tragacanth, gelatin, hydroxypropyl cellulose, etc.; the excipients include, for example, starches, crystalline cellulose, dextrin, lactose, mannitol, sorbitol, anhydrous calcium phosphate, etc.; and the flavors and seasonings include, for example, citric acid, fumaric acid, tartaric acid, menthol, flavors of citrus fruits, etc. These additives other than the polymers are incorporated in an amount of not more than 40% by weight, preferably not more than 20% by weight, based on the whole weight of the preparation in order to avoid deterioration of the release sustaining properties of the present preparation.

In the case of using nifedipine as the active ingredient of the present sustained-release preparation, the nifedipine is incorporated in the form of a solid solution in polyvinylpyrrolidone. That is, in one embodiment of the present preparation containing nifedipine as the active ingredient, the sustained-release preparation comprises a solid solution of nifedipine in polyvinylpyrrolidone in admixture with polyacrylic acid and/or a pharmaceutically acceptable salt thereof and optionally conventional additives as mentioned hereinbefore.

The polyvinylpyrrolidone used for the solid solution is not specified, but preferably has a molecular weight of $1 \times 10^4$ to $4 \times 10^5$ in view of stability of the solid solution. Two or more kinds of solid solution of nifedipine in polyvinylpyrrolidone having different molecular weights may be used. The polyacrylic acid and a salt thereof are the same as mentioned hereinbefore. Besides, the ratio of the solid solution and polyacrylic acid and/or a salt thereof is preferably in the range of 95:5 to 5:95 by weight like in the above-mentioned sustained-release preparation of all other active ingredients.

The solid solution of nifedipine in polyvinylpyrrolidone can be prepared by dissolving nifedipine and an appropriate amount of polyvinylpyrrolidone in an organic solvent (e.g. methyl alcohol, ethyl alcohol, methylene chloride) and then drying the solution, wherein nifedipine is dissolved in polyvinylpyrrolidone as solid state. In the solid solution, nifedipine and polyvinypyrrolidone are contained in the range of 1 to 20 parts by weight of polyvinylpyrrolidone to 1 part by weight of nifedipine.

The sustained-release preparation containing the above solid solution of nifedipine is prepared in the same manner as described hereinbefore, that is, by mixing well the powdery solid solution, polyacrylic acid and/or a pharmaceutically acceptable salt thereof and optionally one or more additives such as lubricants, binding agents, excipients, flavours, seasonings in order to improve the appearance, flavor and taste, and forming the mixture into a suitable shape with a punch, die, or press, or granulating and then press-forming the granules into a suitable shape.

In the above preparation, a small amount of a water-soluble high molecular weight compound may be incorporated in addition to the solid solution and polyacrylic acid and/or a salt thereof in order to promote effectively the release of nifedipine from the solid solution when the preparation is applied. Suitable examples of the water-soluble high molecular weight compound are polyvinylpyrrolidone, polyvinyl alcohol, polyethylene glycol, sodium alginate, alternating copolymer of maleic anhydride and methyl vinyl ether, or the like.

The above sustained-release preparation containing nifedipine solid solution may also be formed into two-layer preparation by combining a layer of the above preparation comprising a nifedipine solid solution and additives with a layer comprising nifedipine and a specific polymer component. That is, another embodiment of the nifedipine-containing sustained-release preparation applicable to mucous membrane in oral cavity of the present invention comprises a layer (I) comprising a solid solution of nifedipine in polyvinylpyrrolidone and a pharmaceutically acceptable carrier, said polyvinylpyrrolidone being contained in an amount of 20 to 80% by weight based on the whole weight of the layer (I), and a layer (II) comprising a solid solution of nifedipine in polyvinylpyrrolidone and polyacrylic acid and/or a pharmaceutically acceptable salt thereof, said solid solution and polyacrylic acid and/or a salt thereof being contained in a ratio of 95:5 to 5:95 by weight, and optionally in admixture with conventional carrier and additives.

The sustained-release preparation comprising two layers is prepared in the same manner as described hereinbefore. However, it is preferable to use different kinds of polyvinylpyrrolidone in the layers (I) and (II). That is, the polyvinylpyrrolidone used for the layer (I) having rapid releasing property has preferably a molecular weight of $1 \times 10^4$ to $1 \times 10^5$, and the polyvinylpyrrolidone used for the layer (II) having late releasing property has preferably a molecular weight of $1 \times 10^5$ to $4 \times 10^5$. Besides, the layer (II) may contain a polyvinylpyrrolidone having a molecular weight of $1 \times 10^4$ to $1 \times 10^5$.

The sustained-release preparation of the present invention is characteristic in that it is easily adhered to mucous membrane in the oral cavity and the adhesion is maintained for a long period of time, for example, for 4 to 24 hours. Besides, it can be kept within the oral cavity without being peeled off even by usual mouth action such as drinking, smoking, eating and speaking. A second characteristic of the present preparation is that the formed preparation is swollen by saliva to become soft, and hence, it does not give any abnormal feeling to the persons to whom the preparation is applied. The third characteristic of the present preparation is that the release of the active ingredient can be sustained in accordance with the viscosity of the base materials. A fourth characteristic of the present preparation is that the dose of each preparation is previously fixed when it is prepared, and hence, there is no difference of dose in each application (not like in an ointment).

A fifth characteristic of the present preparation is that the adhesion and release sustaining property of the preparation can be controlled by appropriately controlling the components, for instance, in case of the sustained-release preparation comprising the polymer components (A) and (B) and an active ingredient, by controlling the ratio of the polymers in the polymer component (A) selected from one or more of polyvinylpyrrolidone, polyvinyl alcohol, polyethylene glycol, alginic acid or a pharmaceutically acceptable salt thereof, and an alternating copolymer of maleic anhydride and methyl vinyl ether, and the polymers in the polymer component (B) selected from one or more of polyacrylic acid and a pharmaceutically acceptable salt thereof. Besides, in case of the preparation comprising the layer (I) and the layer (II), the adhesion and the release sustaining property can also be controlled by controlling the ratio of the layer (I) and the layer (II).

These characteristics of the present invention have experimentally been confirmed as explained hereinafter.

The present invention is illustrated by the following Tests, Reference Examples and Examples, but should not be construed to be limited to these Examples. In the Reference Examples and Examples, the term "part" means a part by weight unless specified otherwise.

Test 1

Adhesion to mucous membrane in mouse peritoneum:

Referring to the accompanying FIGS. 7 and 8, the test method is explained below.

Track field type tablets (6) having various compositions were prepared in the same manner as described in Reference Example 1 hereinafter. A stainless steel hook (7) was fixed onto the tablets (6) with an adhesive. Onto a square acrylic plate (2) (area: 9 cm$^2$) back of mouse peritoneum (5) was fixed with an adhesive. The thus prepared plate was put on a support plate (1) fixed with a hook, and thereon, a packing (3) and a fixing plate (4) were piled, and the four corners thereof were fixed with a screw (8). The surface of the peritoneum (5) was wetted with a small amount of water, and thereon, the above-prepared hooked tablet was put, and then, the tablet was pressed with a load of 1700 g for one minute in order to adhere the tablet to the mouse peritoneum (5). The hook (7) of tablet side was fixed with an upper chuck (8) of a tensiometer and the hook in the supporting plate side (1) was fixed with a lower chuck (9). Water was filled on the mouse peritoneum, and then the hook in the supporting plate side was drawn, and thereby the load by which the peritoneum and tablet were peeled off was measured with the tensiometer (Tensilon UTM/III, manufactured by Toyo Boldwin K.K., Japan), by which the adhesion of teblet at a wet state was measured.

Test 2

Test of dissolution of a medicament: water-soluble azulene:

The test was carried out by using a dissolution tester (manufactured by Toyama Sangyo K.K., Japan).

Test tablets were prepared in the same manner as in Test 1, and one surface of the tablet was wetted, and the track field type tablet was pushed onto the side wall of a 1000 ml vessel at a height of 7.5 cm from the bottom, by which the tablet was fixed in a state that the short diameter side of the tablet was kept horizontal. 37° C. physiological saline solution (900 ml) was added to the vessel, and the solution was stirred at 100 r.p.m. while keeping the temperature at 37° C. Sampling (each time, 3 ml) was done occasionally. At each sampling, a physiological saline solution was supplemented in order to maintain the volume of solution in the vessel at 900 ml. As to the collected samples, optical density at 280 m$\mu$ was measured with a spectrophotometer 220A (manufactured by Hitachi Ltd., Japan). Based on the obtained data, the dissolving amount of a medicament per 1 ml was calculated in the light of a calibration curve which was previously obtained.

Test 3

Test of adhesion onto mucous membrane and abnormal feeling in volunteers:

In the same manner as described in Reference Example 1 hereinafter, test tablets having various compositions (except that azulene (5 parts) was omitted) were prepared. In order to test the adhesion onto the mucous membrane and abnormal feeling, the tablets were adhered to an outer teethridge of an upper back tooth in 14 volunteers. Adhesion was observed for a period until the tablets were peeled off. Abnormal feeling was evaluated by opinionaires which were submitted by each volunteer after testing. Besides, in order to observe effect of drinking and eating, the volunteers acted along the time schedule as shown in Table 1.

REFERENCE EXAMPLE 1

Sodium polyacrylate (PAS-100P ®, manufactured by Teikoku Kagaku Sangyo K.K., Japan) (56 parts), lactose (56 parts), magnesium stearate (0.5 part) and water-soluble azulene powder (5 parts) are mixed and the mixture is tabletted to give track field type tablets (weight: 125 mg, thickness: 1.3 mm, long diameter: 12.4 mm, short diameter: 6.2 mm).

The tablets were subjected to Test 1 (adhesion test) and Test 2 (dissolution test). The results are shown in FIGS. 1 to 6. The data of Reference Example 1 are shown by "a" in FIG. 1 and by "▲ - ▲" in FIGS. 2 to 6.

REFERENCE EXAMPLE 2

Tablets are prepared in the same manner as described in Reference Example 1 except that a mixture (112 parts) of various ratios of hydroxypropyl cellulose (HPC-L ®, manufactured by Nippon Soda, Japan) and polyacrylic acid (Carbopol 934 ®, manufactured by Goodrich Chemical, U.S.A.) is used instead of sodium polyacrylate and lactose.

The tablets were tested as to adhesion (Test 1). The results are shown in FIG. 1, wherein the data of Reference Example 2 is shown by "● - ●".

REFERENCE EXAMPLE 3

Tablets are prepared in the same manner as described in Reference Example 1 except that 112 parts of polyvinylpyrrolidone (PVP K-90 ®, manufactured by Gokyo Sangyo, K.K., Japan), polyvinyl alcohol (Kurare PVA-217 ®, manufactured by Kurare, Japan), polyethylene glycol (special grade of reagent, molecular weight: $2 \times 10^4$, manufactured by Nakai Chemical, Japan), sodium alginate (Dack Algine ®, manufactured by Kamogawa Kasei K.K., Japan), and an alternating copolymer of maleic anhydride-methyl vinyl ether (1:1) (Gantrez AN-169 ®, manufactured by Gokyo Sangyo K.K., Japan), respectively, are used instead of sodium polyacrylate and lactose.

The tablets were tested in the same manner as in Reference Example 1. The results are shown in FIGS. 1 to 6.

In FIG. 1, "b" means data for polyvinylpyrrolidone, "c" means data for polyvinyl alcohol, "d" means data of polyethylene glycol, "e" means data for an alternating copolymer of maleic anhydride-methyl vinyl ether (1:1), "f" means data for sodium alginate.

In FIG. 2, "● - - - ●" means data for polyvinylpyrrolidone.

In FIG. 3, "● - - - ●" means data for polyvinyl alcohol.

In FIG. 4, "● - - - ●" means data for polyethylene glycol.

In FIG. 5, "● - - - ●" means data for an alternating copolymer of maleic anhydride-methyl vinyl ether.

In FIG. 6, "● - - - ●" means data for sodium alginate.

REFERENCE EXAMPLE 4

Tablet are prepared in the same manner as described in Reference Example 1 except that 112 parts of polyacrylic acid (Carbopol 934 ®, manufactured by Goodrich Chemical, U.S.A.) are used instead of sodium polyacrylate and lactose.

The tablets were tested as to adhesion (Test 1). The results are shown in FIG. 1, wherein the data of Reference Example 4 is shown by "g".

REFERENCE EXAMPLE 5

In the same manner as described in Reference Example 1 except that the water-soluble azulene (5 parts) is omitted, the preparation is prepared.

The preparation was subjected to Test 3: adhesion to mucous membrane and abnormal feeling in volunteers. The results are shown in Table 1.

REFERENCE EXAMPLE 6

In the same manner as described in Reference Example 4 except that the water-soluble azulene (5 parts) is omitted, the preparation is prepared.

The preparation was subjected to Test 3: adhesion to mucous membrane and abnormal feeling in volunteers. The results are shown in Table 1.

EXAMPLE 1

Tablets are prepared in the same manner as described in Reference Example 1 except that mixtures (112 parts) of various ratios of polyvinylpyrrolidone (PVP K-90 ®, manufactured by Gokyo Sangyo K.K., Japan) and polyacrylic acid (Carbopol 934 ®, manufactured by Goodrich Chemical, U.S.A.) are used instead of sodium polyacrylate and lactose.

The tablets were tested in the same manner as described in Reference Example 1. The results are shown in FIGS. 1 and 2, together with the results of Reference Examples.

In FIG. 1, "▽ - - - ▽" means the data of polyvinylpyrrolidone/polyacrylic acid.

In FIG. 2, the data of polyvinylpyrrolidone/polyacrylic acid (mixed ratio, 8/2 by weight) are shown by "○—○", the data of those (mixed ratio, 4/6 by weight) are shown by "□—□", and the data of those (mixed ratio, 2/8 by weight) are shown by "□ - - - □".

As is clear from FIG. 1, the preparation of this example was superior to the preparation of sodium polyacrylate/lactose (1:1) in Reference Example 1, to the preparations of various ratios of hydroxypropyl cellulose/polyacrylic acid in Reference Example 2, and to the preparation of polyacrylic acid alone in Reference Example 4 in adhesion. Besides, it is clear that when a small amount of polyacrylic acid is added to polyvinylpyrrolidone, or when a small amount of polyvinylpyrrolidone is added to polyacrylic acid, the adhesion of polyvinylpyrrolidone and polyacrylic acid is improved.

Moreover, as is clear from FIG. 2, the preparation of this example was superior to the preparation of sodium polyacrylate/lactose (1:1) in Reference Example 1 and to the preparation of polyvinylpyrrolidone alone in Reference Example 3 in the release sustaining property.

EXAMPLE 2

Tablets are prepared in the same manner as described in Reference Example 1 except that mixtures (112 parts) of various ratios of polyvinyl alcohol (PVA-217 ®, manufactured by Kurare, Japan) and polyacrylic acid (Carbopol 934 ®, manufactured by Goodrich Chemical, U.S.A.) are used instead of sodium polyacrylate and lactose.

The tablets were tested in the same manner as described in Reference Example 1. The results are shown in FIGS. 1 and 3, together with the results of Reference Examples.

In FIG. 1, "▲—▲" means the data of polyvinyl alcohol/polyacrylic acid.

In FIG. 3, the data of polyvinyl alcohol/polyacrylic acid (mixed ratio, 8/2 by weight) are shown by "○—○", the data of those (mixed ratio, 4/6 by weight) are shown by "□—□", and the data of those (mixed ratio, 2/8 by weight) are shown by "□ - - - □".

As is clear from FIG. 1, the preparation of this example was superior to the preparation of sodium polyacrylate/lactose (1:1) in Reference Example 1, to the preparations of various ratios of hydroxypropyl cellulose/polyacrylic acid in Reference Example 2, and to the preparation of polyacrylic acid alone in Reference Example 4 in adhesion. Besides, it is clear that when a small amount of polyacrylic acid is added to polyvinyl alcohol, or when a small amount of polyvinyl alcohol is added to polyacrylic acid, the adhesion of polyvinyl alcohol and polyacrylic acid is improved.

Moreover, as is clear from FIG. 3, the preparation of this example was superior to the preparation of sodium polyacrylate/lactose (1:1) in Reference Example 1 and to the preparation of polyvinyl alcohol alone in Reference Example 3 in the release sustaining property.

EXAMPLE 3

Tablets are prepared in the same manner as described in Reference Example 1 except that mixtures (112 parts) of various ratios of polyethylene glycol (special grade of reagent, molecular weight: $2 \times 10^4$, manufactured by Nakai Chemical K.K., Japan) and polyacrylic acid (Carbopol 934 ®, manufactured by Goodrich Chemical, U.S.A.) are used instead of sodium polyacrylate and lactose.

The tablets were tested in the same manner as described in Reference Example 1. The results are shown in FIGS. 1 and 4, together with the results of Reference Examples.

In FIG. 1, "○—○" means the data of polyethylene glycol/polyacrylic acid.

In FIG. 4, the data of polyethylene glycol/polyacrylic acid (mixed ratio, 8/2 by weight) are shown by "○—○", the data of those (mixed ratio, 4/6 by weight) are shown by "□ - - - □", and the data of those (mixed ratio, 2/8 by weight) are shown by "□—□".

As is clear from FIG. 1, the preparation of this example was superior to the preparation of sodium polyacrylates/lactose (1:1) in Reference Example 1 and to the preparations of various ratios of hydroxypropyl cellulose/polyacrylic acid in Reference Example 2 in adhesion. Besides, it is clear from FIG. 4 that the preparation of this example was superior to the preparation of sodium polyacrylate/lactose (1:1) in Reference Example 1 and to the preparation of polyvinyl alcohol alone in Reference Example 3 in the release sustaining property.

EXAMPLE 4

Tablets are prepared in the same manner as described in Reference Example 1 except that mixtures (112 parts) of various ratios of an alternating copolymer of maleic anhydride-methyl vinyl ether (1:1) (Gantrez AN- 169 ®, manufactured by Gokyo Sangyo K.K., Japan) and polyacrylic acid (Carbopol 934 ®, manufactured by Goodrich Chemical, U.S.A.) are used instead of sodium polyacrylate and lactose.

The tablets were tested in the same manner as described in Reference Example 1. The results are shown in FIG. 1 and FIG. 5.

In FIG. 1, "Δ - - - Δ" means the data of an alternating copolymer of maleic anhydride-methyl vinyl ether/polyacrylic acid.

In FIG. 5, the data of an alternating copolymer of maleic anhydride-methyl vinyl ether/polyacrylic acid (mixed ratio, 8/2 by weight) are shown by "○ — ○", the data of those (mixed ratio, 4/6 by weight) are shown by "□—□", and the data of those (mixed ratio, 2/8 by weight) are shown by "□ - - - □".

As is clear from FIG. 1, the preparation of this example was superior to the preparation of sodium polyacrylate/lactose (1:1) in Reference Example 1 and to the preparations of various ratios of hydroxypropyl cellulose/polyacrylic acid in Reference Example 2 in adhesion. Besides, it is clear that when a small amount of polyacrylic acid is added to an alternating copolymer of maleic anhydride-methyl vinyl ether, or when a small amount of an alternating copolymer of maleic anhydride-methyl vinyl ether is added to polyacrylic acid, the adhesion of each component alone is improved.

Moreover, as is clear from FIG. 5, the preparation of this example was superior to the preparation of sodium polyacrylate/lactose (1:1) in Reference Example 1 and to the preparation of an alternating copolymer of maleic anhydride-methyl vinyl ether alone in Reference Example 3 in the release sustaining property.

EXAMPLE 5

Preparations are prepared in the same manner as described in Reference Example 1 except that mixtures (112 parts) of various ratios of sodium alginate (Duck Algine ®, manufactured by Kamogawa Kasei K.K., Japan) and polyacrylic acid (Carbopol 934 ®, manufactured by Goodrich Chemical, U.S.A.) are used instead of sodium polyacrylate and lactose.

The preparation were tested in the same manner as described in Reference Example 1. The results are shown in FIGS. 1 and 6, together with the results of Reference Examples.

In FIG. 1, "∇ - - - ∇" means the data of sodium alginate/polyacrylic acid.

In FIG. 6, the data of sodium alginate/polyacrylic acid (mixed ratio, 8/2 by weight) are shown by "○ — ○", the data of those (mixed ratio, 4/6 by weight) are shown by "□—□", and the data of those (mixed ratio, 2/8 by weight) are shown by "□ - - - □".

As is clear from FIG. 1, the preparation of this example was superior to the preparation of sodium polyacrylate/lactose (1:1) in Reference Example 1, to the preparations of various ratios of hydroxypropyl cellulose/polyacrylic acid in Reference Example 2, and to the preparation of polyacrylic acid alone in Reference Example 4 in adhesion. Besides, it is clear from FIG. 6 that the preparation of this example was superior to the preparation of sodium polyacrylate/lactose (1:1) in Reference Example 1 and to the preparation of sodium alginate alone in Reference Example 3 in the release sustaining property.

EXAMPLE 6

Tablets are prepared in the same manner as described in Reference Example 1 except that a mixture of polyvinylpyrrolidone (PVP K-90 ®, manufactured by Gokyo Sangyo K.K., Japan) (33 parts), polyvinyl alcohol (PVA-217C ®, manufactured by Kurare, Japan) (34.2 parts) and polyacrylic acid (Carbopol 934 ®, manufactured by Goodrich Chemical, U.S.A.) (44.8 parts) is used instead of sodium polyacrylate and lactose in Reference Example 1.

The tablets were tested in the same manner as described in Reference Example 1. The results of dissolving out test are shown in FIG. 2.

In FIG. 2, "● — ●" means the data of polyvinylpyrrolidone/polyvinyl alcohol/polyacrylic acid (33:34.2:44.8).

The preparation of this example had an adhesion of 500 g which was superior to the preparation of sodium polyacrylate/lactose (1:1) in Reference Example 1 (adhesion: 15 g), to the preparation of polyacrylic acid alone (adhesion: 310 g), and to the preparations of hydroxypropyl cellulose/polyacrylic acid in Reference Example 2 (as shown in FIG. 1). Besides, it is clear from FIG. 2 that the preparation of this example was superior to the preparation of sodium polyacrylate/lactose (1:1) in Reference Example 1 and to the preparation of polyvinylpyrrolidone alone in Reference Example 3 in the release sustaining property.

EXAMPLE 7

A preparation of mixtures of a component (A) consisting of polyvinylpyrrolidone (PVP K-90 ®, manufactured by Gokyo Sangyo K.K., Japan), polyvinyl alcohol (PVA-217C ®, manufactured by Kurare, Japan), polyethylene ethylene glycol (special grade of reagent, molecular weight: $2 \times 10^4$, manufactured by Nakai Chemical K.K., Japan), an alternating copolymer of maleic anhydride-methyl vinyl ether (1:1) (Gantrez AN-169 ®, manufactured by Gokyo Sangyo K.K., Japan), or sodium alginate (Duck Algine ®, manufactured by Kamogawa Kasei K.K., Japan) (each 56 parts) and a component (B) consisting of polyacrylic acid (Carbopol 934 ®, manufactured by Goodrich Chemical, U.S.A.) (56 parts) wherein the components (A) and (B) are incorporated in the weight ratio of 1:1, which is admixed with magnesium stearate (0.5 part), is prepared in the same manner as described in Reference Example 1 instead of the preparation of Reference Example 1 which comprises sodium polyacrylate (56 parts), lactose (56 parts), magnesium stearate (0.5 part) and water-soluble azulene powder (5 parts).

The preparation was tested in the same manner as described in Reference Examples 5 and 6. The results are shown in Table 1. As is clear from Table 1, the preparation of this example was adhered for a longer period of time than the preparation of sodium acrylate and carriers and had much less abnormal feeling than the preparation of polyacrylic acid alone.

TABLE 1

Test of adhesion to mucous membrane in oral cavity and abnormal feeling in patients Time schedule: 8.00 Start test — 10.00 Drinking tea — 12.00 Lunch — 15.00 Drinking tea — 18.00 Dinner — 21.00 Go to bed — Next day 8.00 Final observation

| Test samples | Run No. | Observation | Final observation | Abnormal feeling |
|---|---|---|---|---|
| Sodium acrylate + lactose (1:1) (Ref. Ex. 5) | 1 | Tablets were completely dissolved by saliva (before 10:00) | — | No |
| | 2 | Tablets were completely dissolved by saliva (around 10:00) | — | No |
| Polyacrylic acid (Ref. Ex. 4) | 3 | — | Remained in final | Very strong (largely swollen in mouth) |
| | 4 | — | Remained in final | Very strong (largely swollen in mouth) |
| Polyvinylpyrrolidone + polyacrylic acid (1:1) (Ex. 7) | 5 | — | Remained in final | No |
| | 6 | — | Remained in final | No |
| Polyvinyl alcohol + polyacrylic acid (1:1) (Ex. 7) | 7 | — | Remained in final | No |
| | 8 | — | Remained in final | No |
| Polyethylene glycol + polyacrylic acid (1:1) (Ex. 7) | 9 | — | Remained in final | |
| | 10 | — | Remained in final | No |
| Maleic anhydride/alternating copolymer of methyl vinyl ether + polyacrylic acid (1:1) (Ex. 7) | 11 | — | Remained in final | No |
| | 12 | — | Remained in final | No |
| Sodium alginate + polyacrylic acid (1:1) (Ex. 7) | 13 | — | Remained in final | No |
| | 14 | — | Remained in final | No |

Test 4

Test of adhesion onto mucous membrane and abnormal feeling in volunteers:

The test was carried out in the same manner as described in Test 3 except that test tablets having various compositions in the same manner as described in Example 8 hereinafter (except that indomethacine sodium salt (5 parts) was omitted) were used, and that the test was done on 24 volunteers.

Test 5

Administration of indomethacin-containing preparation applicable to mucous membrane in oral cavity in beagle dogs:

Male beagle dogs (weighing 8 to 10 kg, one group: 6 dogs) were fasted for 24 hours. A track field type tablet (each one tablet) as prepared in the same manner as described in Example 8 was adhered onto an outer teethridge of an upper back tooth of dogs. At a fixed interval, blood (1.2 ml) was collected from a vein of a foreleg with a syringe which was wetted with 10% heparin. The collected blood was centrifuged at 3000 r.p.m. and at 40° C. for 6 minutes to give blood plasma (0.5 ml), of which the concentration of indomethacin was measured.

To the blood plasma was added a citrate buffer (pH 5.0, 0.5 ml) and further added diethyl ether (2.0 ml). The mixture was shaken for 2 minutes. After centrifuging the mixture at 10,000 r.p.m. for 5 minutes, the upper layer (0.5 ml) was collected and evaporated to dryness at 50° C. The resulting residue was dissolved in acetonitrile (100 μl) which contained an internal standard substance, and the solution was subjected to liquid chromatography with Water's high speed liquid chromatography apparatus under the following conditions:

Column: μ-Bondapak C 18 (Water's), one column
Mobile phase: 0.01M acetate buffer (pH 4.0)/acetonitrile=50/50
Flow rate: 1.0 ml/minute
Detecting wavelength: 254 mμ
Detecting sensitivity: 0.02 a.u.f.s.
Internal standard substance: phenylbutazone

EXAMPLE 8

Polyvinylpyrrolidone (28 parts), lactose (28 parts), magnesium stearate (0.25 part) and indomethacin sodium salt (2.5 parts) are homogeneously mixed, and the mixture is tabletted to form a layer (I), wherein polyvinylpyrrolidone is contained in a ratio of 48% by weight based on the whole weight of the layer (I).

Separately, polyacrylic acid (44.8 parts), polyvinylpyrrolidone (11.2 parts), magnesium stearate (0.25 part) and indomethacin sodium salt (2.5 parts) are mixed, and the mixture is put on the layer (I) prepared above, and the resultant is tabletted to give a track field type, two-layer tablet (weight: 125 mg, thickness: 1.3 mm, long diameter: 12.4 mm, short diameter: 6.2 mm) (hereinafter, referred to as "Preparation No. 1").

In the same manner as described above, various tablets (Preparation Nos. 2 to 24) as shown in Table 2 are prepared.

TABLE 2

| Preparation No. | Layer | Lactose (a) | Polyacrylic acid (b) | Polyvinyl-pyrrolidone (c) | Magnesium stearate | Indomethacin sodium salt | (a)/(c) | (c)/(b) |
|---|---|---|---|---|---|---|---|---|
| 1 | (I) | 28 | | 28 | 0.25 | 2.5 | 1/1 | |
|   | (II) | | 44.8 | 11.2 | " | " | | 2/8 |
| 2 | (I) | 28 | | 28 | 0.25 | 2.5 | 1/1 | |
|   | (II) | | 33.6 | 22.4 | " | " | | 4/6 |
| 3 | (I) | 28 | | 28 | 0.25 | 2.5 | 1/1 | |
|   | (II) | | 11.2 | 44.8 | " | " | | 8/2 |
| 4 | (I) | 39.2 | | 16.8 | 0.25 | 2.5 | 7/3 | |
|   | (II) | | 44.8 | 11.2 | " | " | | 2/8 |
| 5 | (I) | 39.2 | | 16.8 | 0.25 | 2.5 | 7/3 | |
|   | (II) | | 33.6 | 22.4 | " | " | | 4/6 |
| 6 | (I) | 39.2 | | 16.8 | 0.25 | 2.5 | 7/3 | |
|   | (II) | | 11.2 | 44.8 | " | " | | 8/2 |
| | | | | Polyvinyl alcohol (c) | | | | |
| 7 | (I) | 28 | | 28 | 0.25 | 2.5 | 1/1 | |
|   | (II) | | 44.8 | 11.2 | " | " | | 2/8 |
| 8 | (I) | 28 | | 28 | 0.25 | 2.5 | 1/1 | |
|   | (II) | | 33.6 | 22.4 | " | " | | 4/6 |
| 9 | (I) | 28 | | 28 | 0.25 | 2.5 | 1/1 | |
|   | (II) | | 11.2 | 44.8 | " | " | | 8/2 |
| 10 | (I) | 39.2 | | 16.8 | 0.25 | 2.5 | 7/3 | |
|    | (II) | | 44.8 | 11.2 | " | " | | 2/8 |
| 11 | (I) | 39.2 | | 16.8 | 0.25 | 2.5 | 7/3 | |
|    | (II) | | 33.6 | 22.4 | " | " | | 4/6 |
| 12 | (I) | 39.2 | | 16.8 | 0.25 | 2.5 | 7/3 | |
|    | (II) | | 11.2 | 44.8 | " | " | | 8/2 |
| | | | | Sodium alginate (c) | | | | |
| 13 | (I) | 28 | | 28 | 0.25 | 2.5 | 1/1 | |
|    | (II) | | 44.8 | 11.2 | " | " | | 2/8 |
| 14 | (I) | 28 | | 28 | 0.25 | 2.5 | 1/1 | |
|    | (II) | | 33.6 | 22.4 | " | " | | 4/6 |
| 15 | (I) | 28 | | 28 | 0.25 | 2.5 | 1/1 | |
|    | (II) | | 11.2 | 44.8 | " | " | | 8/2 |
| 16 | (I) | 39.2 | | 16.8 | 0.25 | 2.5 | 7/3 | |
|    | (II) | | 44.8 | 11.2 | " | " | | 2/8 |
| 17 | (I) | 39.2 | | 16.8 | 0.25 | 2.5 | 7/3 | |
|    | (II) | | 33.6 | 22.4 | " | " | | 4/6 |
| 18 | (I) | 39.2 | | 16.8 | 0.25 | 2.5 | 7/3 | |
|    | (II) | | 11.2 | 44.8 | " | " | | 8/2 |
| | | | | Alternating copolymer of maleic anhydride/methyl vinyl ether (c) | | | | |
| 19 | (I) | 28 | | 28 | 0.25 | 2.5 | 1/1 | |
|    | (II) | | 44.8 | 11.2 | " | " | | 2/8 |
| 20 | (I) | 28 | | 28 | 0.25 | 2.5 | 1/1 | |
|    | (II) | | 33.6 | 22.4 | " | " | | 4/6 |
| 21 | (I) | 28 | | 28 | 0.25 | 2.5 | 1/1 | |
|    | (II) | | 11.2 | 44.8 | " | " | | 8/2 |

TABLE 2-continued

| Preparation No. | Layer | Lactose (a) | Polyacrylic acid (b) | Magnesium stearate | Indomethacin sodium salt | (a)/(c) | (c)/(b) |
|---|---|---|---|---|---|---|---|
| 22 | (I) | 39.2 |  | 16.8 | 0.25 | 2.5 | 7/3 |
|  | (II) |  | 44.8 | 11.2 | " | " |  | 2/8 |
| 23 | (I) | 39.2 |  | 16.8 | 0.25 | 2.5 | 7/3 |
|  | (II) |  | 33.6 | 22.4 | " | " |  | 4/6 |
| 24 | (I) | 39.2 |  | 16.8 | 0.25 | 2.5 | 7/3 |
|  | (II) |  | 11.2 | 44.8 | " | " |  | 8/2 |

The tablets (Preparation Nos. 1 to 24) were tested as to adhesion by Test 1 wherein the layer (II) was adhered onto the mouse peritoneum. The results are shown in FIG. 9.

In the figure, "∇-∇" means the data of polyvinylpyrrolidone/polyacrylic acid (Preparation Nos. 1 to 6), "◇...◇" means the data of polyvinyl alcohol/polyacrylic acid (Preparation Nos. 7 to 12), "⦿...⦿" means the data of sodium alginate/polyacrylic acid (Preparation Nos. 13 to 18), and "Δ-Δ" means the data of an alternating copolymer of maleic anhydride-methyl vinyl ether/polyacrylic acid (Preparation Nos. 19 to 24).

Preparation Nos. 3, 5, 8, 12, 14, 18, 21, and 23 among the preparations in Table 2 were tested as to the change of plasma level of indomethacin sodium salt when adhered to mucous membrane in oral cavity in beagle dogs according to Test 5. The results are shown in FIGS. 10 and 11.

In FIG. 10, "●—●" is the data of Preparation No. 3, "○—○" is the data of Preparation No. 5, "■--■" is the data of Preparation No. 8, and "□--□" is the data of Preparation No. 12.

In FIG. 11, "●—●" is the data of Preparation No. 14, "○—○" is the data of Preparation No. 18, "❘--❘" is the data of Preparation No. 21, and "Δ--Δ" is the data of Preparation No. 23.

REFERENCE EXAMPLE 7

Polyvinylpyrrolidone (56 parts), lactose (56 parts), magnesium stearate (0.5 part) and indomethacin sodium salt (5 parts) are mixed, and the mixture is tabletted to give a track field type tablet (weight: 125 mg, thickness: 1.3 mm, long diameter: 12.4 mm, short diameter: 6.2 mm).

The tablet was tested as to the change of plasma level of indomethacin sodium salt according to Test 5. The results are shown in FIG. 12.

Other tablets are prepared in the same manner as described above except that polyvinyl alcohol, sodium alginate or an alternating copolymer of maleic anhydride-methyl vinyl ether (1:1) is used instead of polyvinylpyrrolidone. These tablets were also tested as to the change of plasma level of indomethacin sodium salt likewise. The results are shown in FIG. 12.

In FIG. 12, "∇...∇" is the data of polyvinylpyrrolidone, "❘-❘" is the data of polyvinyl alcohol, "❘...❘" is the data of sodium alginate, and "Δ-Δ" is the data of an alternating copolymer of maleic anhydride-methyl vinyl ether.

REFERENCE EXAMPLE 8

Polyvinylpyrrolidone (5.6 parts), lactose (50.4 parts), magnesium stearate (0.25 part) and indomethacin sodium salt (2.5 parts) are homogeneously mixed, and the mixture is tabletted to form a layer (I), wherein polyvinylpyrrolidone is contained in a ratio of 9.53% by weight based on the whole weight of the layer (I).

Separately, a mixture of polyvinylpyrrolidone and polyacrylic acid (mixed ratio: 10/0, 5/5, or 0/10) (56 parts), magnesium stearate (0.25 part) and indomethacin sodium salt (2.5 parts) are mixed, and the mixture is put on the layer (I) prepared above, and the resultant is tabletted to give a track field type, two-layer tablet (weight: 125 mg, thickness: 1.3 mm, long diameter: 12.4 mm, short diameter: 6.2 mm).

Other two-layer tablets are prepared in the same manner as described above except that polyvinyl alcohol, sodium alginate, or an alternating copolymer of maleic anhydride-methyl vinyl ether is used instead of polyvinylpyrrolidone in the layers (I) and (II).

These two-layer tablets were tested as to the change of plasma level of indomethacin sodium salt when the layer (II) of the tablets was adhered to mucous membrane in oral cavity in beagle dogs (6 dogs) according to Test 5. The results are shown in FIGS. 13 to 16.

REFERENCE EXAMPLE 9

Figure 1:
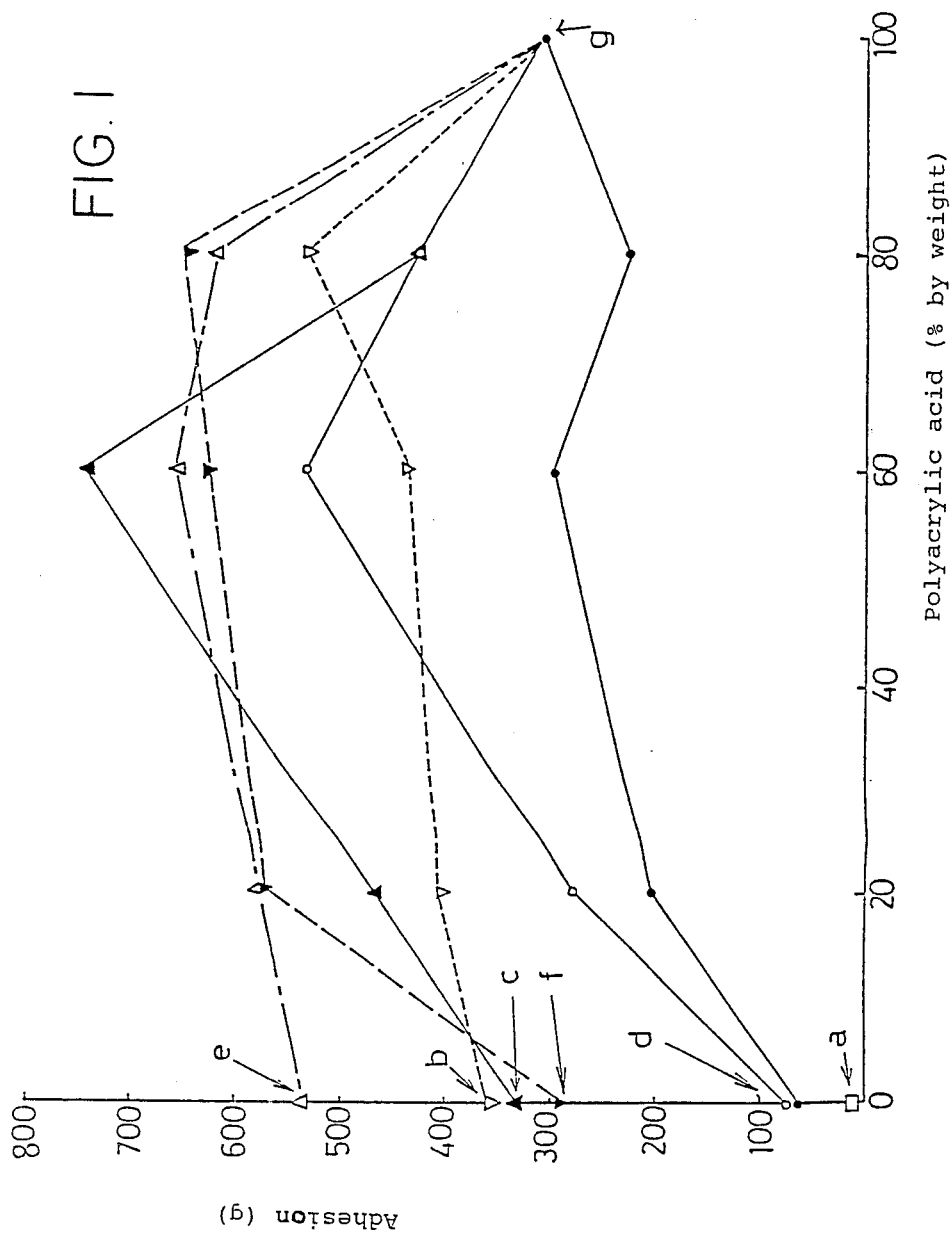
Figure 2:
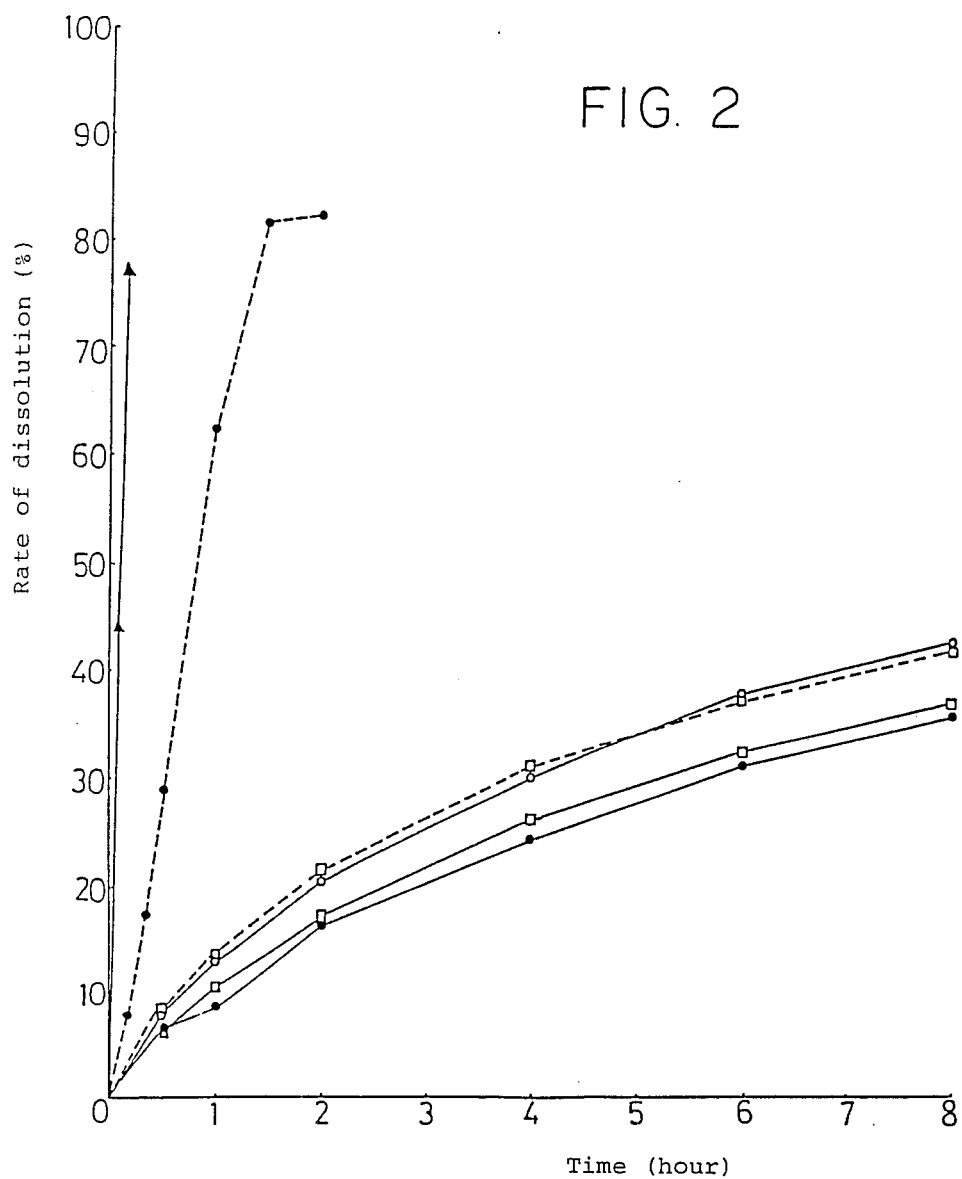
Figure 3:
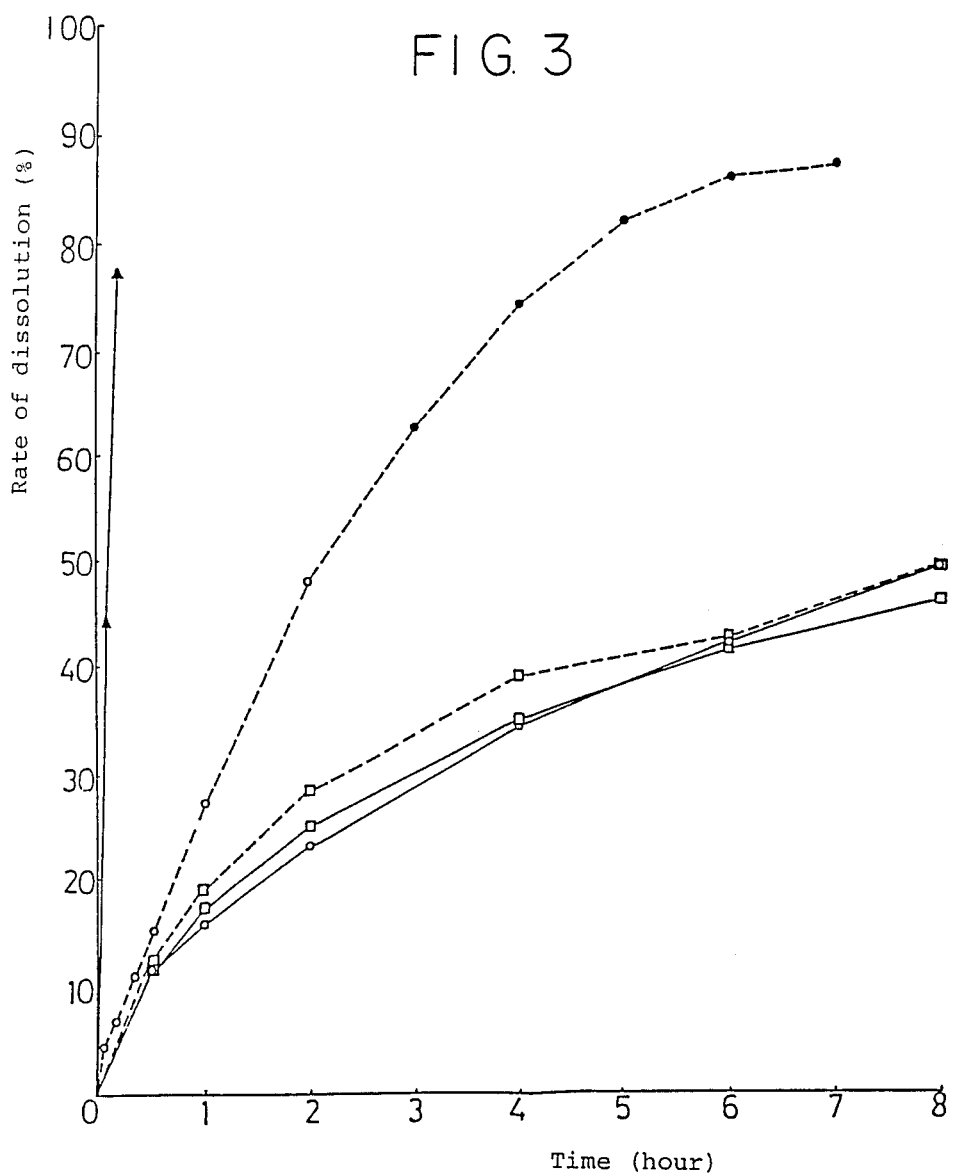
Figure 4:
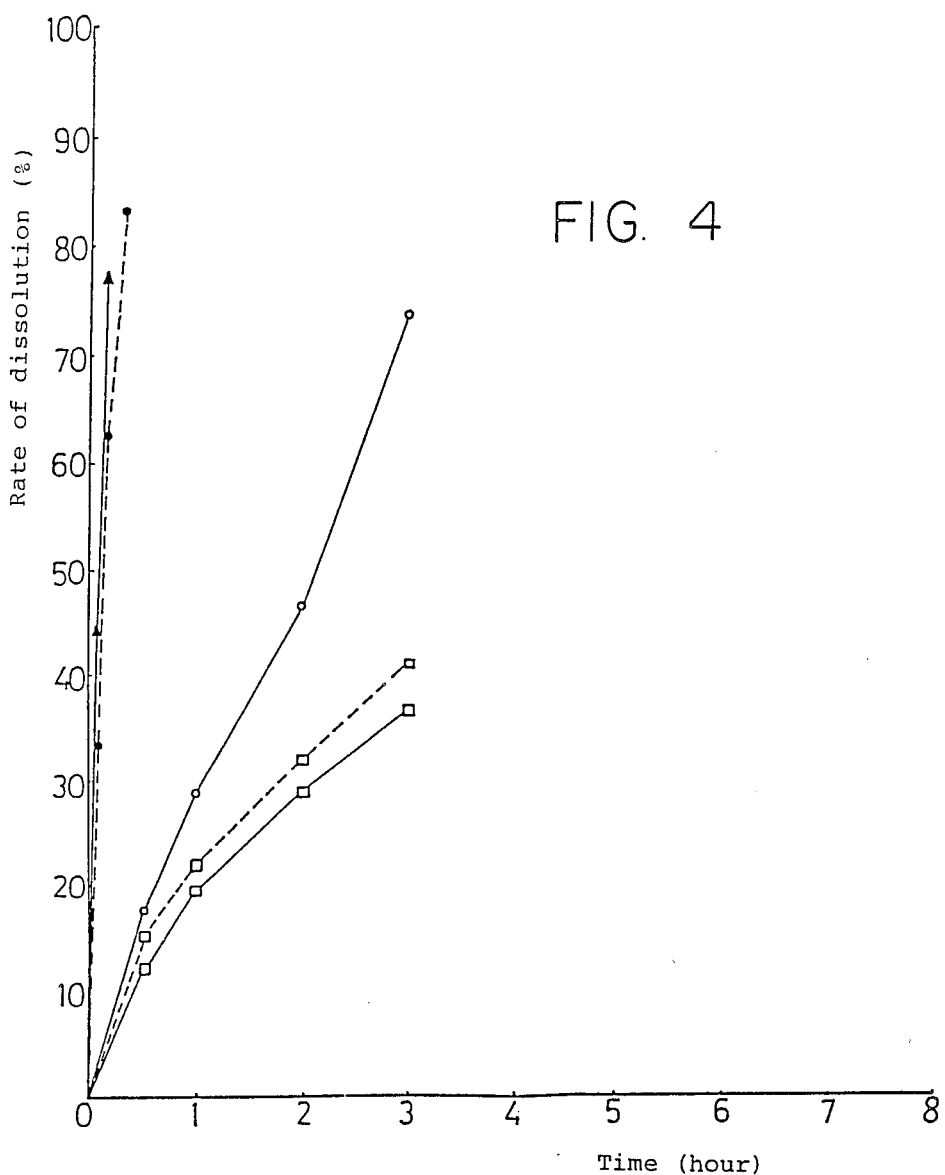
Figure 5:
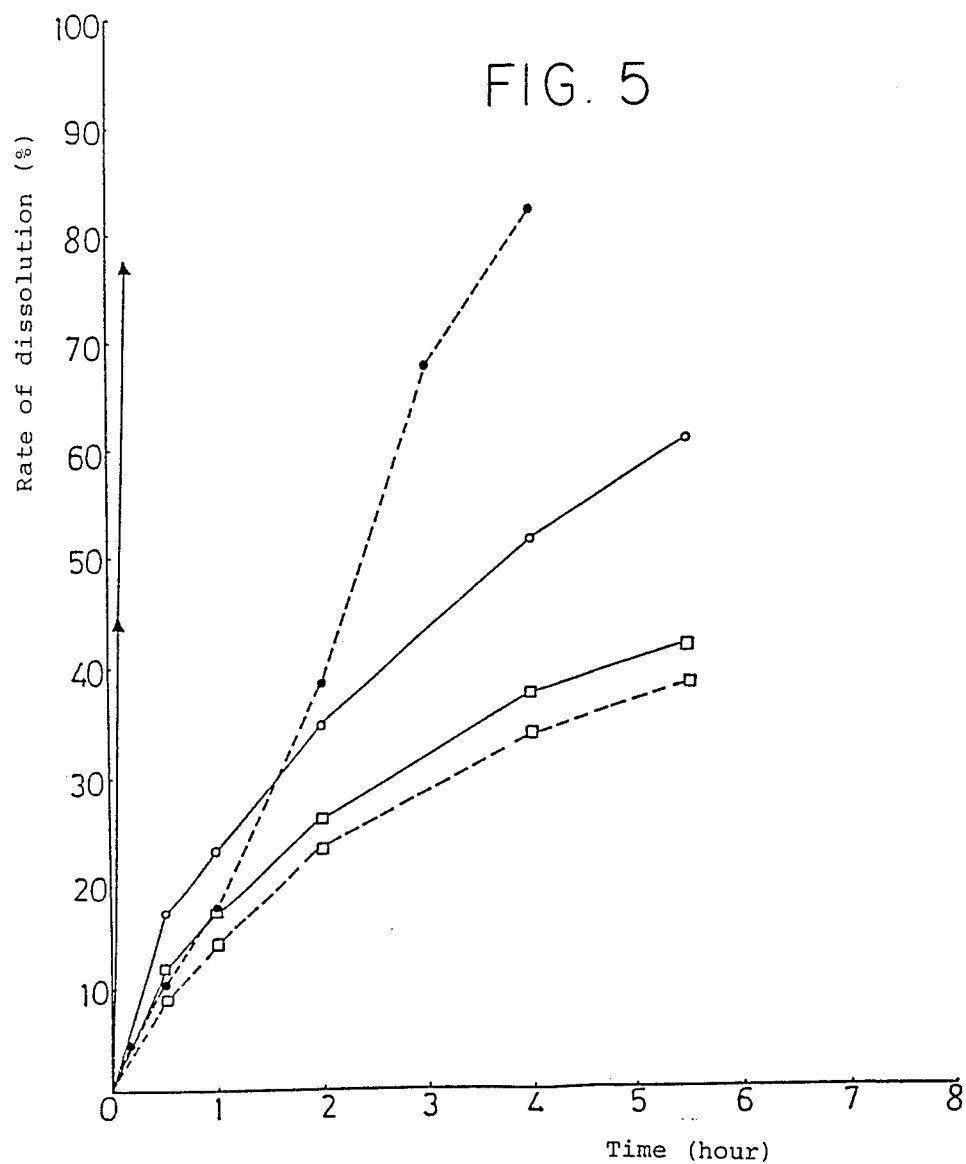
Figure 6:
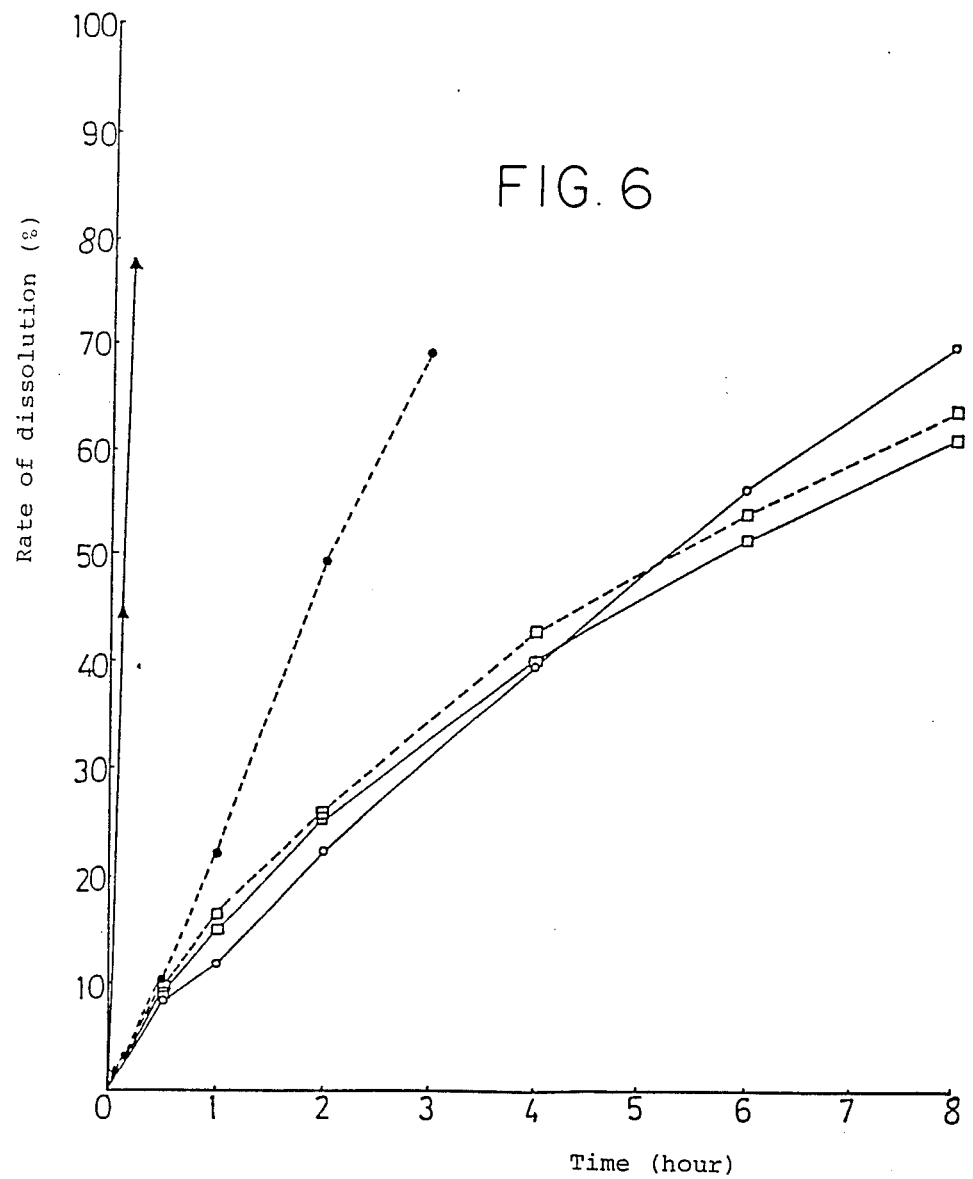
Figure 9:
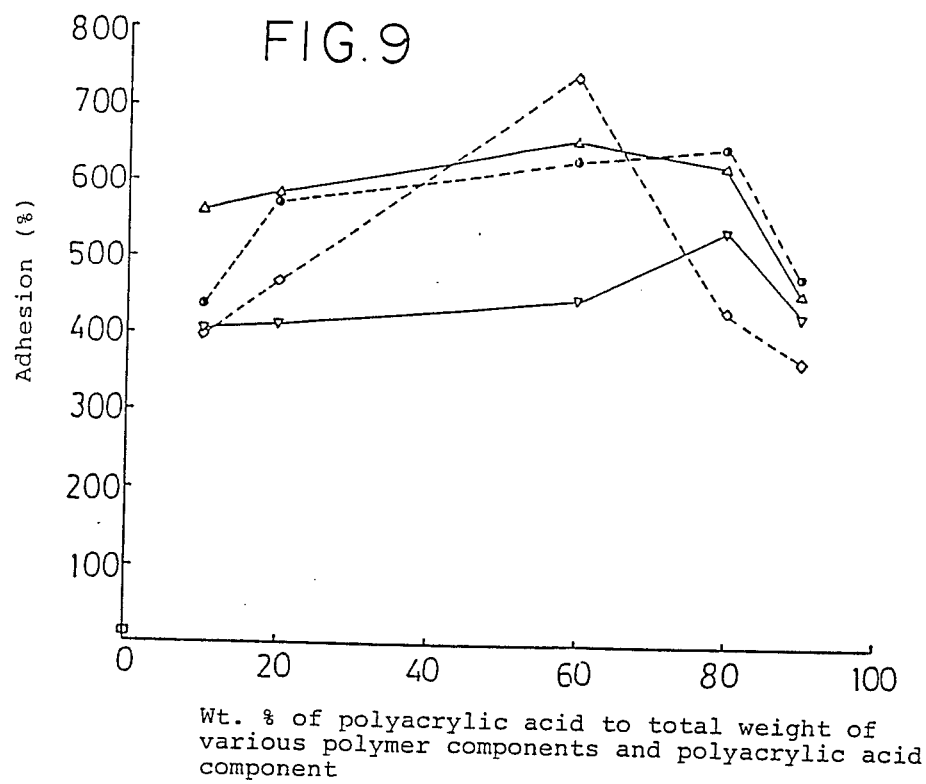
Figure 10:
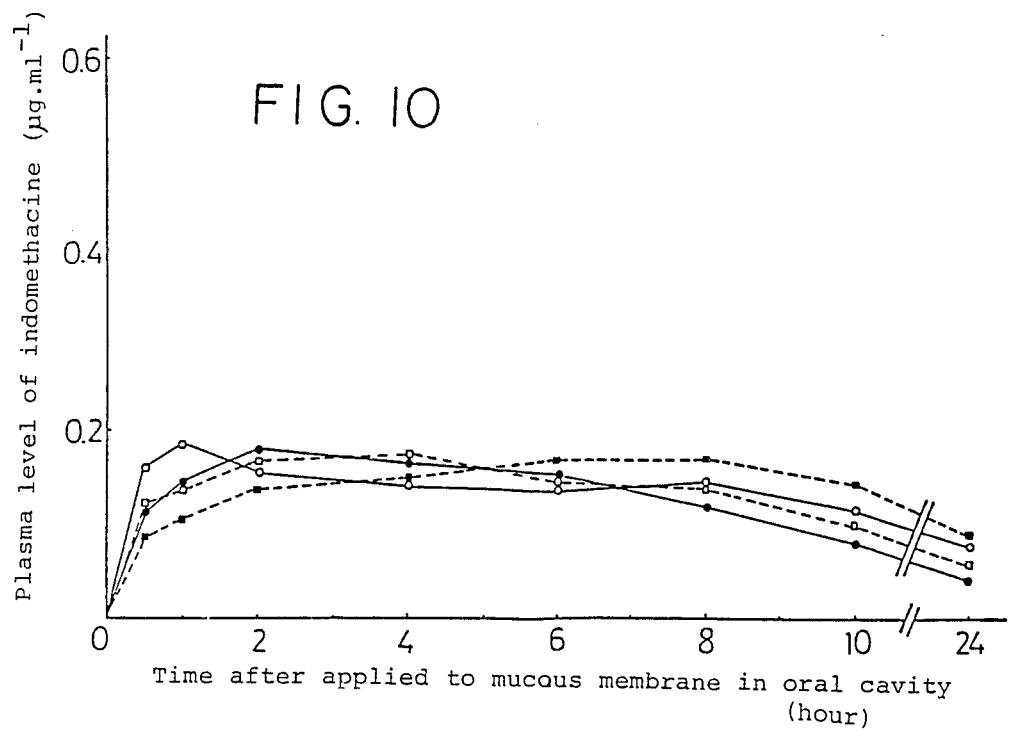
Figure 11:
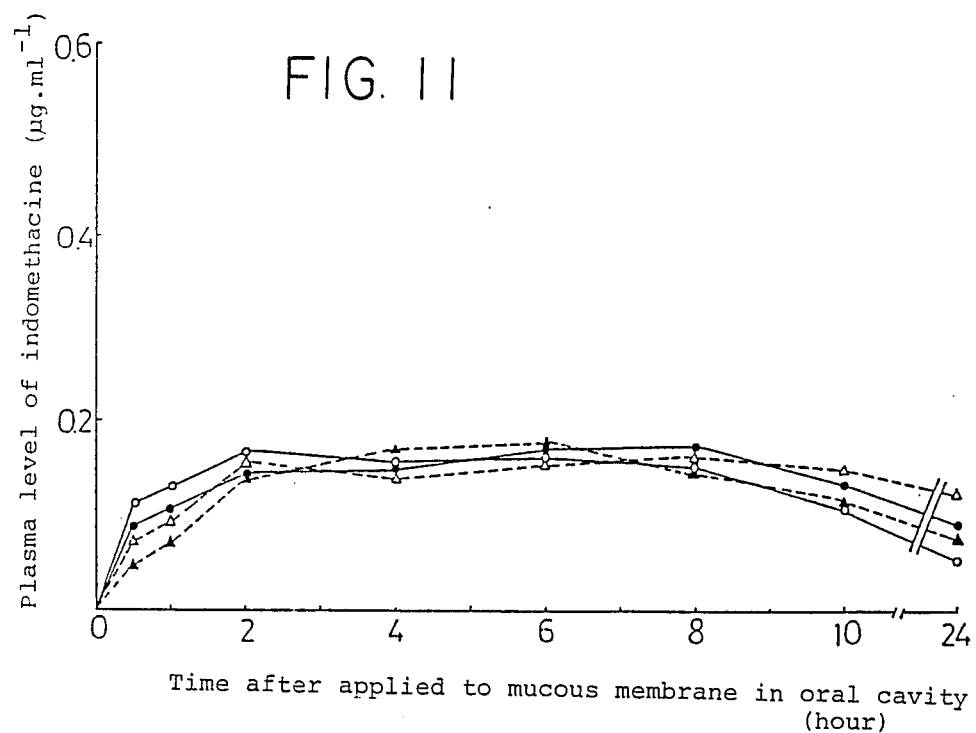

Polyvinylpyrrolidone (28 parts), lactose (28 parts), magnesium stearate (0.25 part) and indomethacin sodium salt (2.5 parts) are homogeneously mixed, and the mixture is tabletted to form a layer (I).

Separately, polyvinylpyrrolidone (56 parts), magnesium stearate (6.25 part) and indomethacin sodium salt (2.5 parts) are mixed, and the mixture is put on the layer (I) prepared above, and the resultant is tabletted to give a track field type, two-layer tablet (weight: 125 mg, thickness: 1.3 mm, long diameter: 12.4 mm, short diameter: 6.2 mm).

Other two-layer tablets are prepared in the same manner as described above except that polyvinyl alcohol, sodium alginate, or an alternating copolymer of maleic anhydride-methyl vinyl ether (1:1) is used instead of polyvinylpyrrolidone in the layers (I) and (II).

These two-layer tablets were tested as to the change of plasma level of indomethacin sodium salt according to Test 5. The results are shown in FIG. 17.

Figure 17:
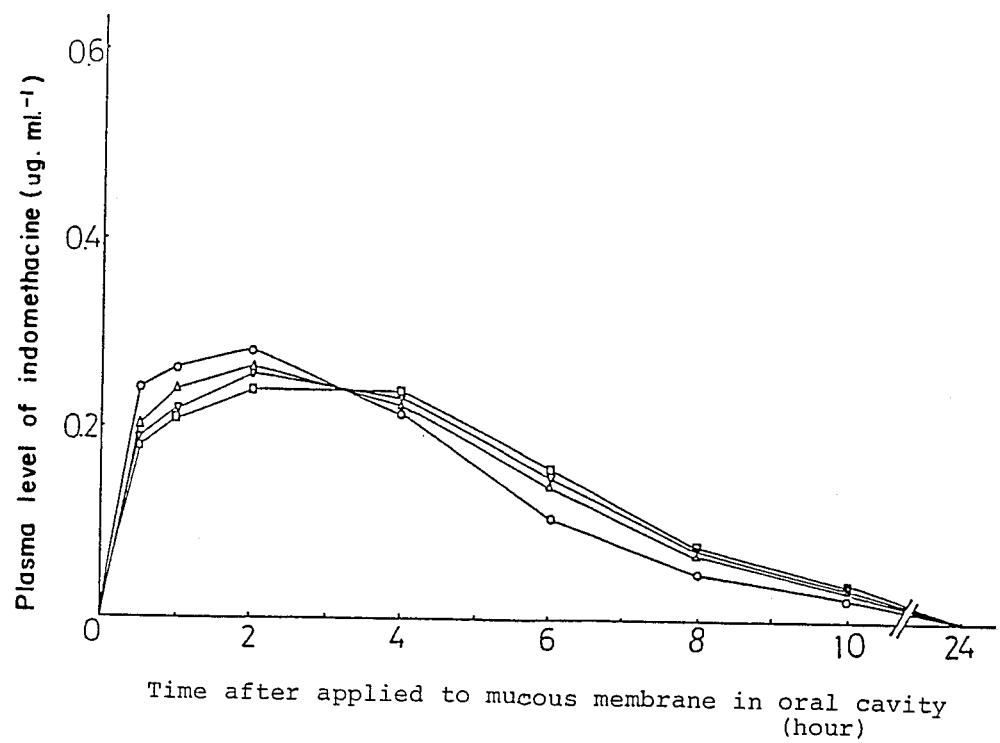

In FIG. 17, "o - o" shows the data for the two-layer tablets containing polyvinylpyrrolidone/lactose (1/1 by weight) in the layer (I) and polyvinylpyrrolidone alone in the layer (II), "□-□" shows the data for the two-layer tablets containing polyvinyl alcohol/lactose (1/1 by weight) in the layer (I) and polyvinyl alcohol alone in the layer (II), "Δ-Δ" shows shows the data for the two-layer tablets containing sodium alginate/lactose (1/1 by weight) in the layer (I) and sodium alginate alone in the layer (II), and "∇-∇" shows the data for the two-layer tablets containing an alternating copolymer of maleic anhydride-methyl vinyl ether (1:1)/lactose (1/1 by weight) in the layer (I) and an alternating copolymer of maleic anhydride-methyl vinyl ether (1:1) alone in the layer (II).

As is clear from FIGS. 10 to 17, the preparation of the present invention can release the medicament at a fixed rate for a long period of time, and hence is excellent as a sustained-release preparation.

Figure 12:
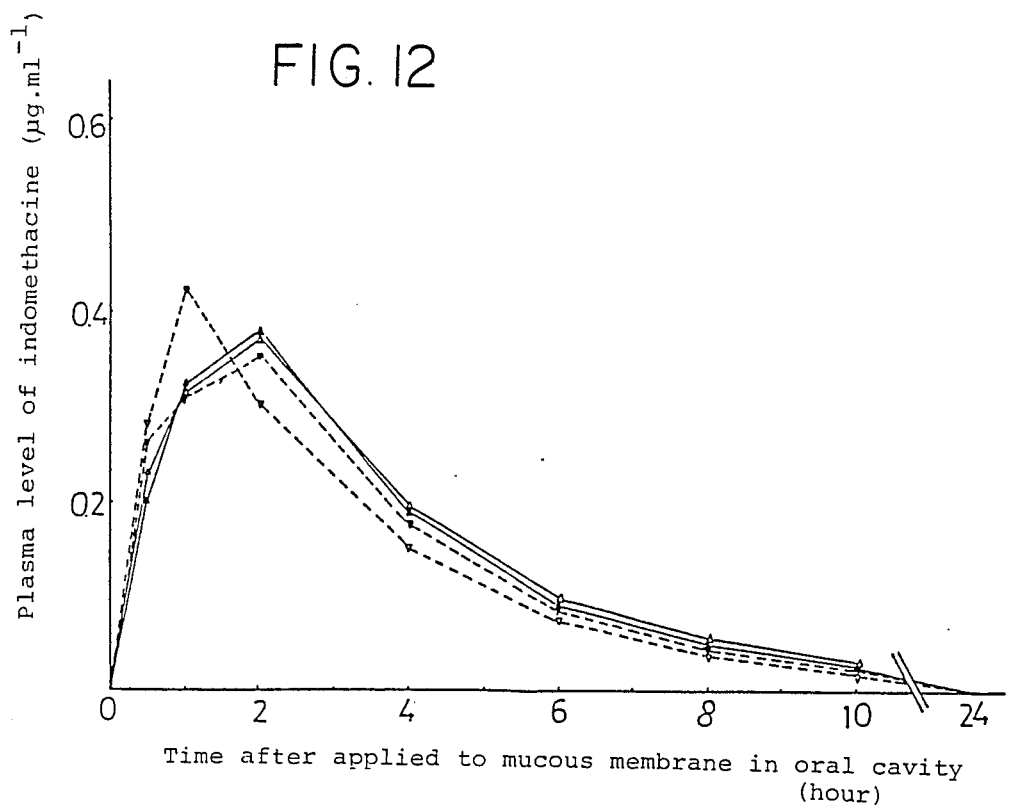
Figure 13:
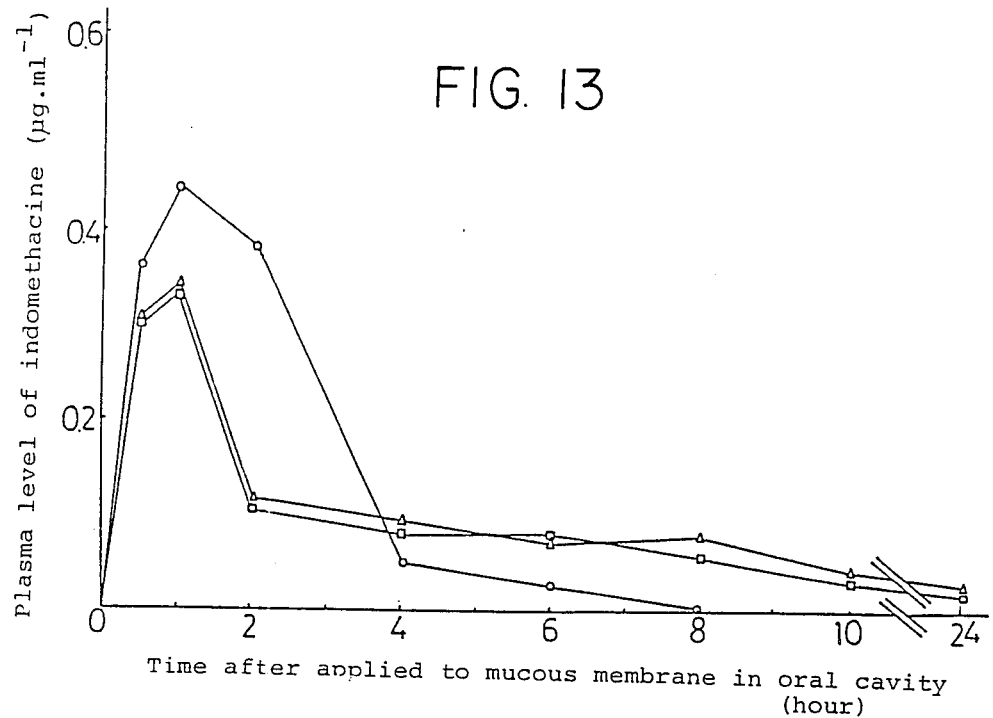
FIG. 13 shows the data of the two-layer tablets containing polyvinylpyrrolidone/lactose (1/9 by weight) in the layer (I), wherein "○-○", "Δ-Δ" and "□-□" are the data for the two-layer tablets containing polyvinylpyrrolidone/polyacrylic acid (10/0, 5/5, and 0/10 by weight) in the layer (II), respectively.
Figure 14:
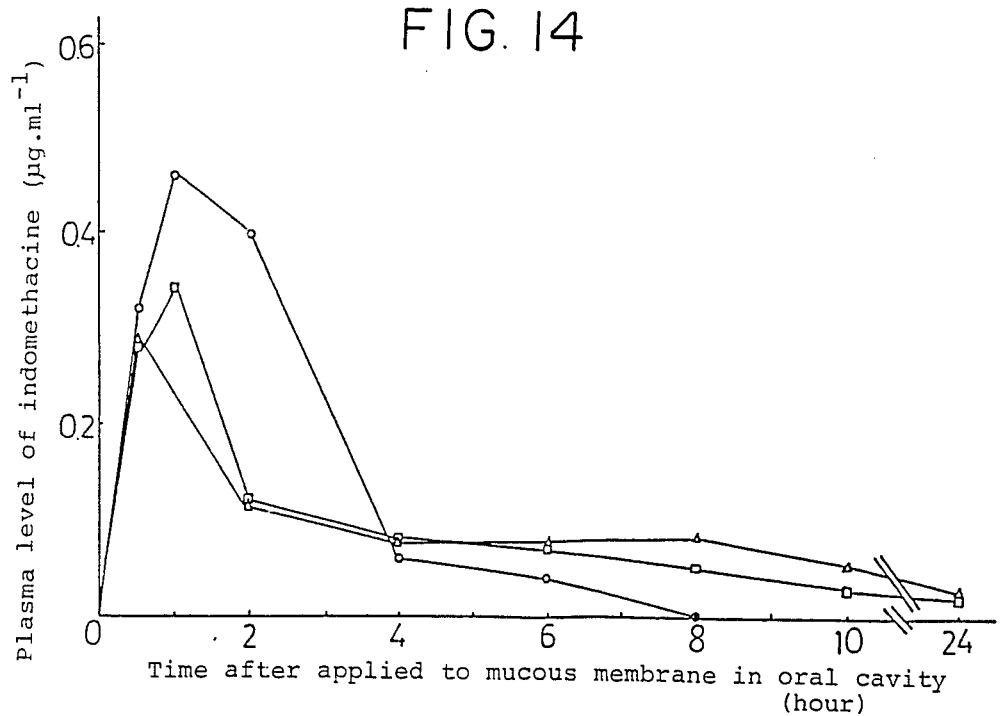
FIG. 14 shows the data for the two-layer tablets containing polyvinyl alcohol/lactose (1/9 by weight) in the layer (I), wherein "○-○", "Δ-Δ" and "□-□" are the data for the two-layer tablets containing polyvinyl alcohol/polyacrylic acid (10/0, 5/5, and 0/10 by weight) in the layer (II), respectively.
Figure 15:
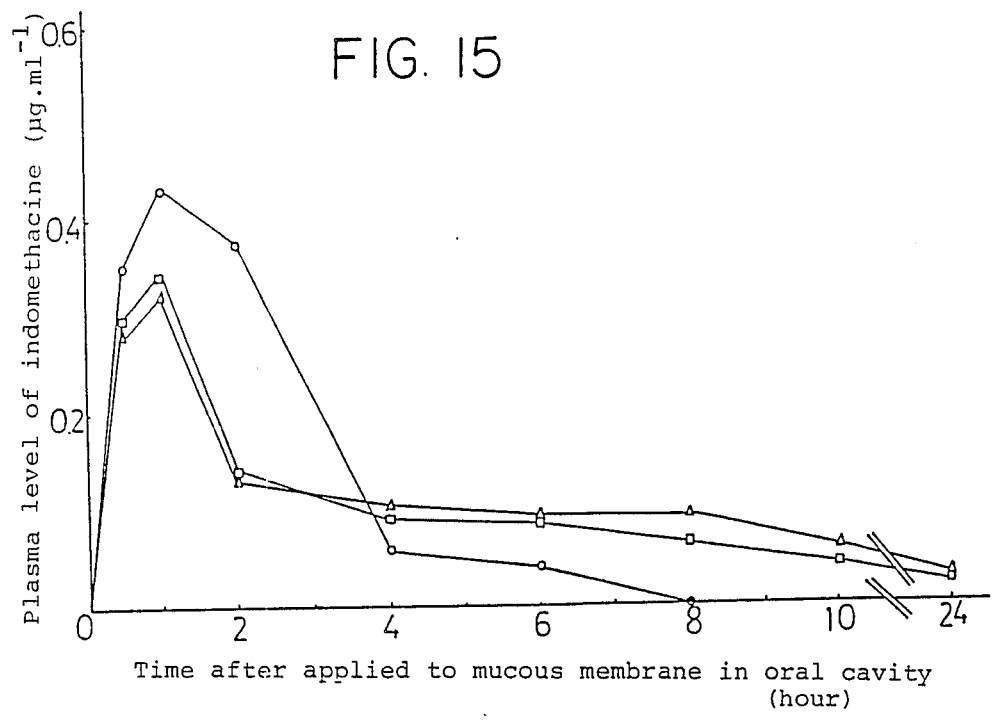
FIG. 15 shows the data for the two-layer tablets containing sodium alginate/lactose (1/9 by weight) in the layer (I), wherein "○-○", "Δ-Δ" and "□-□" are the data for the two-layer tablets containing sodium alginate/polyacrylic acid (10/0, 5/5, and 0/10 by weight) in the layer (II), respectively.
Figure 16:
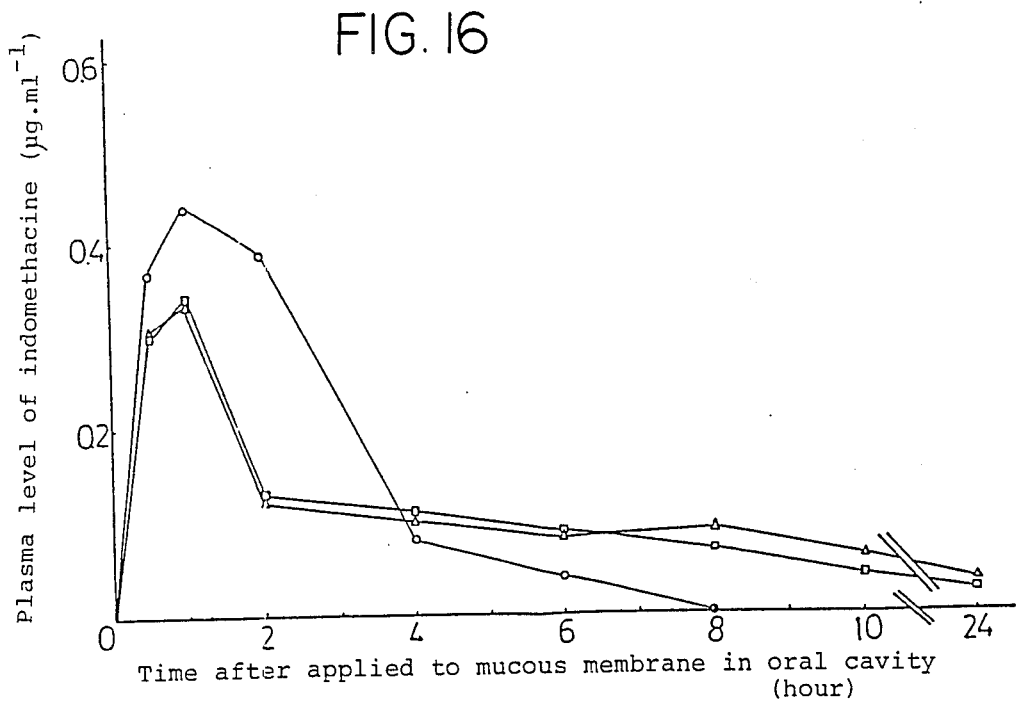
FIG. 16 shows the data for the two-layer tablets containing an alternating copolymer of maleic anhydride-methyl vinyl ether/lactose (1/9 by weight) in the layer (I), wherein "○-○", "Δ-Δ" and "□-□" are the data for the two-layer tablets containing an alternating copolymer of maleic anhydride-methyl vinyl ether/polyacrylic acid (10/0, 5/5, and 0/10 by weight) in the layer (II), respectively.

On the contrary, the preparation of Reference Example 7 which consists of the layer (I) alone has insufficient release sustaining property (cf. FIG. 12).

Besides, in the preparation of Reference Example 8 wherein the polymer component selected from polyvinylpyrrolidone, polyvinyl alcohol, alginic acid or a pharmaceutically acceptable salt thereof, or an alternating copolymer of maleic anhydride-methyl vinyl ether is contained in an amount of less than 20% by weight based on the whole weight of the layer (I) (cf. FIGS. 13 to 16), and in the preparation of Reference Example 9 wherein the layer (II) contains no polyacrylic acid (cf. FIG. 17), they show too high plasma level of active ingredient at the first stage of administration.

EXAMPLE 9

In the same manner as described in Example 8, there are prepared preparations having the same components as the preparation Nos. 2, 3, 8, 9, 14, 15, 20 and 21 as shown in Table 2 except that no indomethacin is contained.

The preparations were tested as to the adhesion onto mucous membrane in oral cavity and abnormal feeling in volunteers according to Test 4 wherein the layer (II) of the two-layer tablets was adhered onto an outer teethridge of an upper back tooth in the volunteers. The results are shown in Table 3.

REFERENCE EXAMPLE 10

Polyvinylpyrrolidone (28 parts), lactose (28 parts) and magnesium stearate (0.25 part) are homogeneously mixed, and the mixture is tabletted to form a layer (I).

Separately, polyacrylic acid (56 parts) and magnesium stearate (0.25 part) are mixed, and the mixture is put on the layer (I) prepared above, and the resultant combination is tabletted to give a track field type, two-layer tablet (weight: 125 mg, thickness: 1.3 mm, long diameter: 12.4 mm, short diameter: 6.2 mm).

Other two-layer tablets are prepared in the same manner as described above except that polyvinyl alcohol, an alternating copolymer of maleic anhydride-methyl vinyl ether (1:1) or sodium alginate is used instead of polyvinylpyrrolidone.

These two-layer tablets were tested as to the adhesion onto mucous membrane in oral cavity and abnormal feeling in volunteers according to Test 4. The results are shown in Table 3.

TABLE 3

| | | | | | |
|---|---|---|---|---|---|
| \multicolumn{6}{l}{Test of adhesion to mucous membrane in oral cavity and abnormal feeling in patients} |
| Example No. | Layer | Test samples Components | Run No. | Observation after 24 hours from the start of test | Abnormal feeling |
| Ref. Example 10 | (I) (II) | Polyvinylpyrrolidone + lactose (1:1) Polyacrylic acid | 1 | Both layer (I) and layer (II) are remained | Yes (largely swollen in mouth) |
| | (I) (II) | Polyvinyl alcohol + lactose (1:1) Polyacrylic acid | 2 | The same above | The same above |
| | (I) (II) | An alternating copolymer of maleic anhydride-methyl vinyl ether + lactose (1:1) Polyacrylic acid | 3 | The same above | the same above |
| | (I) (II) | Sodium alginate + lactose (1:1) Polyacrylic acid | 4 | The same above | The same above |
| Example 9 | (I) (II) | Polyvinylpyrrolidone + lactose (1:1) Polyvinylpyrrolidone + polyacrylic acid (4:6) | 5 | Both layer (I) and layer (II) are remained | No |
| | (I) (II) | Polyvinylpyrrolidone + lactose (1:1) Polyvinylpyrrolidone + polyacrylic acid (8:2) | 6 | The same above | The same above |
| | (I) (II) | Polyvinyl alcohol + lactose (1:1) Polyvinyl alcohol + polyacrylic acid (4:6) | 7 | The same above | The same above |
| | (I) (II) | Polyvinyl alcohol + lactose (1:1) Polyvinyl alcohol + polyacrylic acid (8:2) | 8 | The same above | The same above |
| | (I) (II) | An alternating copolymer of maleic anhydride-methyl vinyl ether + lactose (1:1) An alternating copolymer of maleic anhydride-methyl vinyl ether + polyacrylic acid (4:6) | 9 | The same above | the same above |
| | (I) | An alternating copolymer of maleic | 10 | Both layer (I) | No |

TABLE 3-continued

| Example No. | Layer | Test samples Components | Run No. | Observation after 24 hours from the start of test | Abnormal feeling |
|---|---|---|---|---|---|
| | | anhydride-methyl vinyl ether + lactose (1:1) | | and layer (II) are remained | |
| | (II) | An alternating copolymer of maleic anhydride-methyl vinyl ether + polyacrylic acid (8:2) | | | |
| | (I) | Sodium alginate + lactose (1:1) | 11 | The same above | The same above |
| | (II) | Sodium alginate + polyacrylic acid (4:6) | | | |
| | (I) | Sodium alginate + lactose (1:1) | 12 | The same above | The same above |
| | (II) | Sodium alginate + polyacrylic acid (8:2) | | | |

As is clear from Table 3, the preparations of the present invention can be adhered onto the mucous membrane in oral cavity for a long period of time and do not cause any abnormal feeling when applied.

Test 6

Administration of nifedipine-containing preparation applicable to mucous membrane in oral cavity in beagle dogs:

Male beagle dogs (weighing 8 to 10 kg, one group: 6 dogs) were fasted for 24 hours. A track field type tablet (each one tablet) as prepared in the same manner as described in Reference Example 11 was adhered onto an outer teethridge of an upper back tooth of dogs. At a fixed interval, blood (2.5 ml) was collected from a vein of a foreleg with a syringe which was wetted with 10% heparin. The collected blood was centrifuged at 3000 r.p.m. and at 4° C. for 6 minutes to give blood plasma (1.0 ml), of which the concentration of nifedipine was measured.

To the blood plasma was added a borax-NaOH buffer (pH 10.0, 1.0 ml) and further added toluene (1.0 ml) containing an internal standard substance. The mixture was shaken for 10 minutes. After centrifuging the mixture at 3,000 r.p.m. and at 20° C. for 5 minutes, the upper toluene layer was collected, and the solution was subjected to gas chromatography with a gas chromatography apparatus with an electron captured detector (Yanagimoto G2800-ECD) under the following conditions:

Column: OV-17, 2% Chromosorb W (AW-DMCS)
Column temperature: 270° C.
Injector temperature: 270° C.
Detector temperature: 290° C.
Pressure of carrier gas: 0.9 kg/cm$^2$
Pressure of bleeding gas: 0.79 kg/cm$^2$
Discharging voltage: 195 V
Internal standard substance: diphenyl phthalate Test 7

Test of adhesion onto mucous membrane and abnormal feeling in volunteers:

The two-layer tablets having various compositions as prepared in the same manner as described in Example 13 hereinafter were used. In order to test the adhesion onto the mucous membrane and abnormal feeling, the layer (II) of tablets were adhered to an outer teethridge of an upper back tooth in 6 volunteers (two volunteers for each preparation). Observation was carried out for 8 hours without restricting the usual action of the volunteers, such as eating and drinking.

REFERENCE EXAMPLE 11

A single-layer tablet having only the layer (I):

Nifedipine (10 parts) and polyvinylpyrrolidone (molecular weight: 4×10$^4$) (57.5 parts) are dissolved in a mixture of ethanol/methylene chloride (1:1) (700 parts), and the mixture is spread onto a glass plate, dried at 40° C. overnight to give a solid solution of nifedipine in polyvinylpyrrolidone. The thus-obtained solid solution is pulverized with a freezer mill to give fine powder. The fine powder is mixed with D-mannitol (57.5 parts) and the mixture is tabletted to give track field type tablets (weight: 125 mg, thickness: 1.3 mm, long diameter: 12.4 mm, short diameter: 6.2 mm) which contain nifedipine in an amount of 10 mg per one tablet.

Figure 18:
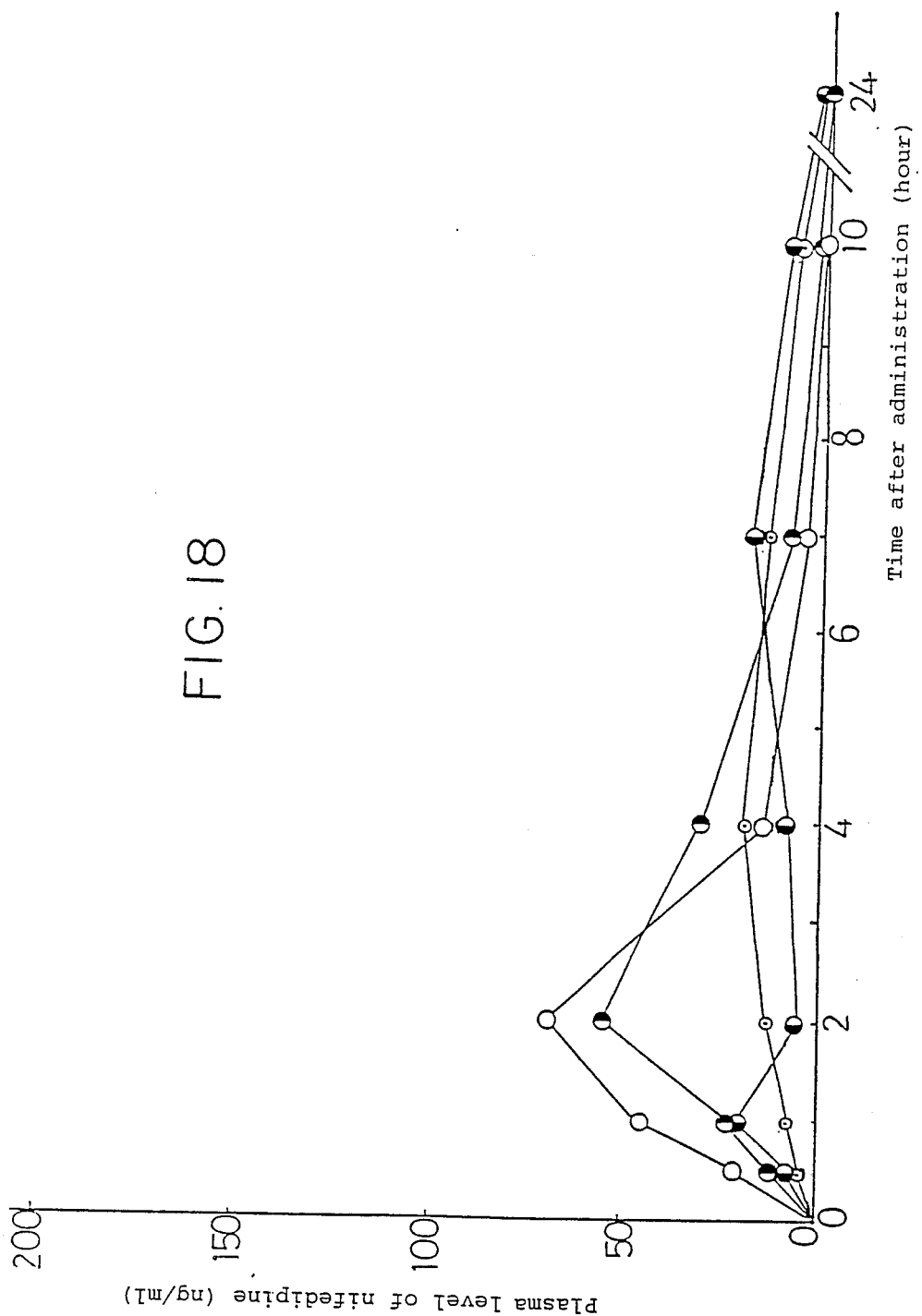

The tablets were tested as to the change of plasma level of nifedipine when the tablets were adhered onto an outer teethridge of an upper back tooth of beagle dogs according to Test 6. The results are shown in FIG. 18. In FIG. 18, the data of Reference Example 11 are shown by "-○-".

REFERENCE EXAMPLE 12

A two-layer tablet containing polyvinylpyrrolidone of less than 20% by weight in the layer (I):

A powdery solid solution prepared from nifedipine (3 parts) and polyvinylpyrrolidone (molecular weight: 4×10$^4$) (9 parts) is mixed with D-mannitol (50.5 parts), and the mixture is tabletted to form the layer (I) wherein nifedipine is contained in an amount of 3 mg per one tablet. On to the layer (I), a mixture of a solid solution prepared from nifedipine (7 parts) and polyvinylpyrrolidone (molecular weight: 36×10$^4$) (28 parts) with polyacrylic acid (27.5 parts) is pressed to form a layer (II) on the layer (I), in said layer (II) nifedipine being contained in an amount of 7 mg per one tablet, and thereby, there are obtained two-layer tablets having the same size as those in Reference Example 11.

The tablets which contain nifedipine in an amount of 10 mg per one tablet were tested in the same manner as in Reference Example 11 wherein the layer (II) of the tablets were adhered onto an outer teethridge of an upper back tooth of beagle dogs. The results are shown in FIG. 18, wherein the data of Reference Example 12 are shown by "-◊-".

REFERENCE EXAMPLE 13

A two-layer tablet containing polyvinylpyrrolidone of more than 80% by weight in the layer (I):

A powdery solid solution prepared from nifedipine (3 parts) and polyvinylpyrrolidone (molecular weight: 4×10$^4$) (56.25 parts) is mixed with D-mannitol (3.25 parts), and the mixture is tabletted to form the layer (I) wherein nifedipine is contained in an amount of 3 mg per one tablet. On to the layer (I), a mixture of a solid solution prepared from nifedipine (7 parts) and polyvinylpyrrolidone (molecular weight: $36 \times 10^4$) (28 parts) with polyacrylic acid (27.5 parts) is pressed to form a layer (II) on the layer (I), in said layer (II) nifedipine being contained in an amount of 7 mg per one tablet, and thereby, there are obtained two-layer tablets having the same size as those in Reference Example 11.

The tablets which contain nifedipine in an amount of 10 mg per one tablet were tested in the same manner as in Reference Example 12 wherein the layer (II) of the tablets were adhered onto an outer teethridge of an upper back tooth of beagle dogs. The results are shown in FIG. 18, wherein the data of Reference Example 13 are shown by "-⊖-".

REFERENCE EXAMPLE 14

A two-layer tablet werein the layer (II) consists of only solid solution:

A powdery solid solution prepared from nifedipine (3 parts) and polyvinylpyrrolidone (molecular weight: $4 \times 10^4$) (29.75 parts) is mixed with D-mannitol (29.75 parts), and the mixture is tabletted to form the layer (I) wherein nifedipine is contained in an amount of 3 mg per one tablet. On to the layer (I), a powdery solid solution prepared from nifedipine (7 parts) and polyvinylpyrrolidone (molecular weight: $36 \times 10^4$) (55.5 parts) is pressed to give two-layer tablets which contain nifedipine in an amount of 10 mg per one tablet.

The tablets were tested in the same manner as in Reference Example 12. The results are shown in FIG. 18, wherein the data of Reference Example 14 are shown by "-◐-".

EXAMPLE 10

A powdery solid solution prepared from nifedipine (3 parts) and polyvinylpyrrolidone (molecular weight: $4 \times 10^4$) (29.75 parts) is mixed with D-mannitol (29.75 parts), and the mixture is tabletted to form the layer (I). On to the layer (I), a mixture of a solid solution prepared from nifedipine (7 parts) and polyvinylpyrrolidone (molecular weight: $36 \times 10^4$) (35 parts) with polyacrylic acid (20.5 parts) is pressed to form a layer (II), by which there are obtained two-layer tablets which contain nifedipine in an amount of 10 mg per one tablet.

Figure 19:
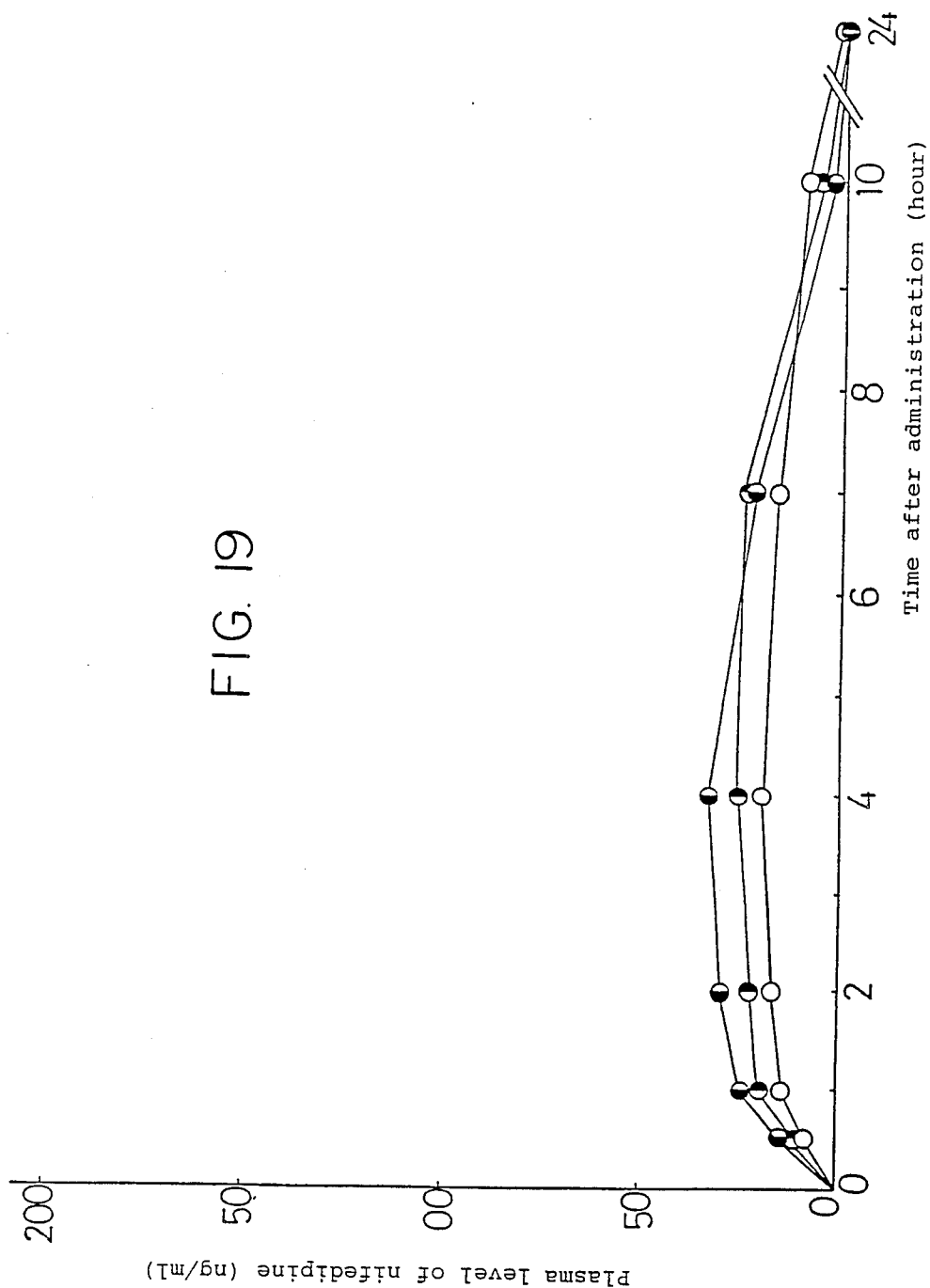

The tablets were tested in the same manner as in Reference Example 12. The results are shown in FIG. 19, wherein the data of Example 10 are shown by "-○-".

EXAMPLE 11

In the same manner as described in Example 10 except the following compositions are used instead of the compositions in Example 10, there are obtained two-layer tablets which contain nifedipine in an amount of 10 mg per one tablet.

| Layer (I): | Nifedipine, 5 parts<br>Polyvinylpyrrolidone<br>(molecular weight: $4 \times 10^4$)<br>28.75 parts<br>D-Mannitol, 28.75 parts | } Solid solution |
| --- | --- | --- |
| Layer (II): | Nifedipine, 5 parts<br>Polyvinylpyrrolidone<br>(molecular weight: $36 \times 10^4$)<br>42.5 parts<br>Polyacrylic acid, 15 parts | } Solid solution |

The tablets were tested likewise. The results are shown in FIG. 19, wherein the data of Example 11 are shown by "-◑-".

EXAMPLE 12

In the same manner as described in Example 10 except the following compositions are used instead of the compositions in Example 10, there are obtained two-layer tablets which contain nifedipine in an amount of 10 mg per one tablet.

| Layer (I): | Nifedipine, 5 parts<br>Polyvinylpyrrolidone<br>(molecular weight: $4 \times 10^4$)<br>39 parts<br>D-Mannitol, 18.5 parts | } Solid solution |
| --- | --- | --- |
| Layer (II): | Nifedipine, 5 parts<br>Polyvinylpyrrolidone<br>(molecular weight: $36 \times 10^4$)<br>34 parts<br>Polyacrylic acid, 23.5 parts | } Solid solution |

The tablets were tested likewise. The results are shown in FIG. 19, wherein the data of Example 12 are shown by "-○-".

As is clear from the comparison of the results of Examples as shown in FIG. 19 with the results of Reference Examples as shown in FIG. 18, the preparation of the present invention can maintain a fixed plasma level of the active ingredient for a longer period of time.

EXAMPLE 13

Three two-layer tablets are prepared in the same manner as described in Examples 10, 11 and 12 except that a powdery mixture of lactose and polyvinylpyrrolidone instead of the solid solution of nifedipine in polyvinylpyrrolidone.

The tablets were tested as to adhesion and abnormal feeling likewise, wherein each tablet was administered to two volunteers. As a result, all tablets showed an excellent adhesion for 8 hours or longer without any abnormal feeling.

REFERENCE EXAMPLE 15

Nifedipine (1 part) and polyvinylpyrrolidone (11.5 parts) are dissolved in a mixture of ethanol/methylene chloride (1:1) (125 parts), and the mixture is spread onto a glass plate, dried at 40° C. overnight to give a solid solution of nifedipine in polyvinylpyrrolidone. The thus-obtained solid solution is pulverized with a freezer mill, and the mixture is tabletted to give track filed type tablets (weight: 125 mg, thickness: 1.3 mm, long diameter: 12.4 mm, short diameter: 6.2 mm).

Figure 20:
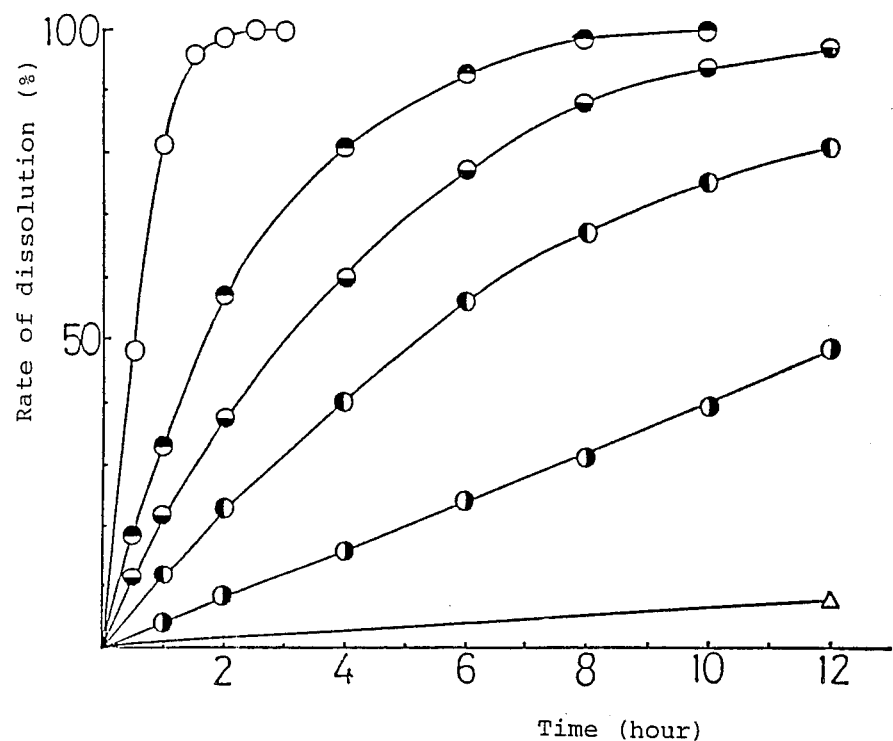
Figure 21:
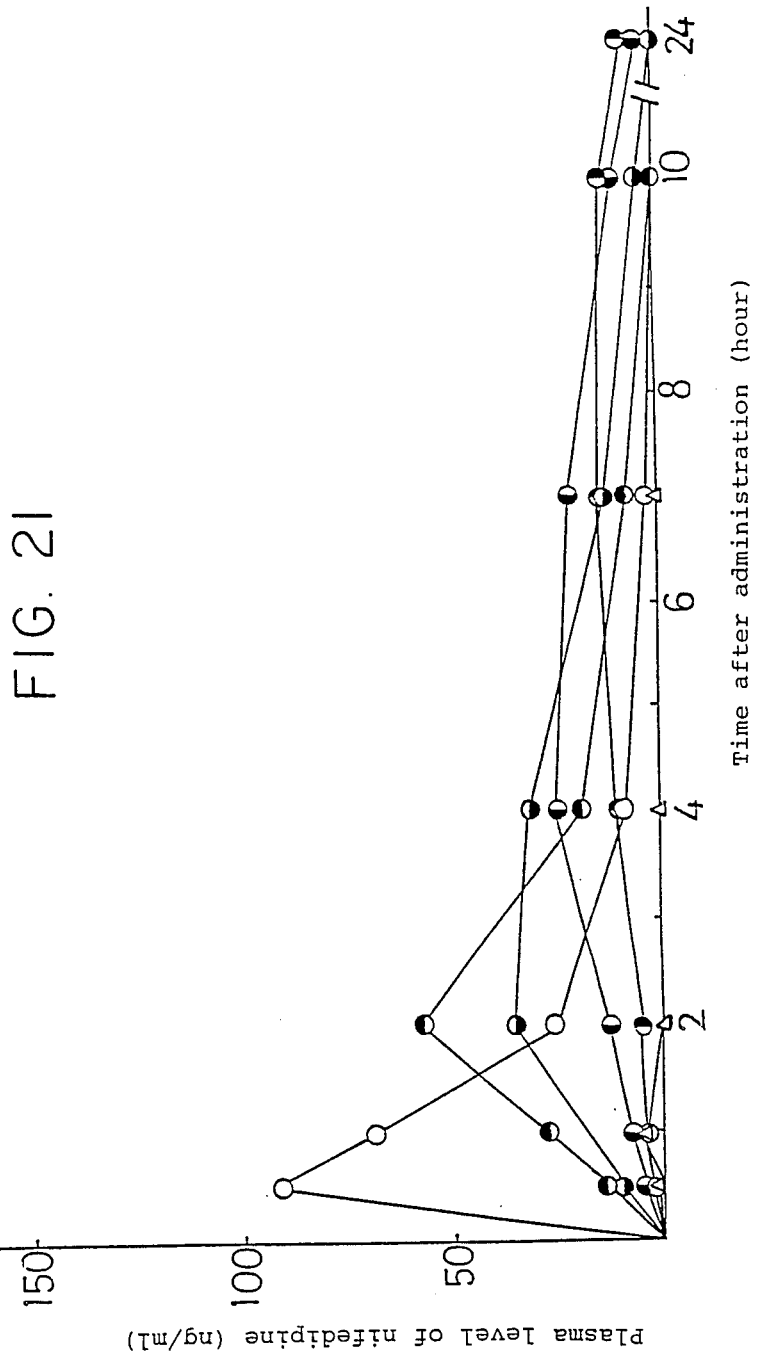

The tablets were tested as to the adhesion by Test 1, the dissolving out by Test 2 and administration to beagle dogs by Test 6. The results are shown in Table 4, FIGS. 20 and 21. In FIGS. 20 and 21, the data of Reference Example 15 are shown by "-○-".

REFERENCE EXAMPLE 16

In the same manner as described in Reference Example 15, similar tablets are prepared by tabletting a powdery mixture of nifedipine (1 part) and polyvinylpyrrolidone (11.5 parts).

The tablets were tested as to the adhesion by Test 1, the dissolution by Test 2 and administration to beagle dogs by Test 6. The results are shown in Table 4, FIGS. 20 and 21. In FIGS. 20 and 21, the data of Reference Example 16 are shown by "-△-".

EXAMPLE 14

In the same manner as described in Reference Example 15, a solid solution is prepared from nifedipine (10 parts) and polyvinylpyrrolidone (102.5 parts). The thus-obtained solid solution is pulverized, and the powdery solid solution (112.5 parts) is mixed with polyacrylic acid (Carbopol 934®, manufactured by Goodrich Chemical, U.S.A.) (12.5 parts), and the mixture is tabletted to give tablets similar to those in Reference Example 15.

The tablets were tested as to the adhesion by Test 1, the dissolution by Test 2 and administration to beagle dogs by Test 6. The results are shown in Table 4, FIGS. 20 and 21. In FIGS. 20 and 21, the data of Example 14 are shown by "-◐-".

EXAMPLE 15

In the same manner as described in Reference Example 15, a solid solution is prepared from nifedipine (10 parts) and polyvinylpyrrolidone (90 parts). The thus-obtained solid solution is pulverized, and the powdery solid solution (100 parts) is mixed with polyacrylic acid (Carbopol 934®, manufactured by Goodrich Chemical, U.S.A.) (25 parts), and the mixture is tabletted to give tablets similar to those in Reference Example 15.

The tablets were tested as to the adhesion by Test 1, the dissolution by Test 2 and administration to beagle dogs by Test 6. The results are shown in Table 4, FIGS. 20 and 21. In FIGS. 20 and 21, the data of Example 15 are shown by "-◐-".

EXAMPLE 16

In the same manner as described in Reference Example 15, a solid solution is prepared from nifedipine (10 parts) and polyvinylpyrrolidone (65 parts). The thus-obtained solid solution is pulverized, and the powdery solid solution (75 parts) is mixed with polyacrylic acid (Carbopol 934®, manufactured by Goodrich Chemical, U.S.A.) (50 parts), and the mixture is tabletted to give tablets similar to those in Reference Example 15.

The tablets were tested likewise. The results are shown in Table 4, FIGS. 20 and 21. In FIGS. 20 and 21, the data of Example 16 are shown by "-◐-".

EXAMPLE 17

In the same manner as described in Reference Example 15, a solid solution is prepared from nifedipine (10 parts) and polyvinylpyrrolidone (40 parts). The thus-obtained solid solution is pulverized, and the powdery solid solution (50 parts) is mixed with polyacrylic acid (Carbopol 934®, manufactured by Goodrich Chemical, U.S.A.) (75 parts), and the mixture is tabletted to give tablets similar to those in Reference Example 15.

The tablets were tested likewise. The results are shown in Table 4, FIGS. 20 and 21. In FIGS. 20 and 21, the data of Example 17 are shown by "-◐-".

TABLE 4

| | Ref. Ex. 15 | Ref. Ex. 16 | Example 14 | Example 15 | Example 16 | Example 17 |
|---|---|---|---|---|---|---|
| Composition | Nifedipine/polyvinylpyrrolidone (1/11.5) only solid solution | Nifedipine/polyvinylpyrrolidone (1/11.5) Powdery mixture | Nifedipine/polyvinylpyrrolidone (1/10.25) Solid solution (112.5 parts) + polyacrylic acid (12.5 parts) | Nifedipine/polyvinylpyrrolidone (1/9) Solid solution (100 parts) + polyacrylic acid (25 parts) | Nifedipine/polyvinylpyrrolidone (1/6.5) Solid solution (75 parts) + polyacrylic acid (50 parts) | Nifedipine/polyvinylpyrrolidone (1/4) Solid solution (50 parts) + polacrylic acid (75 parts) |
| Adhesion (g/cm$^2$) | 62 | 56 | 322 | 356 | 438 | 547 |

As is clear from Table 4, FIGS. 20 and 21, the preparation of the present invention shows excellent adhesion, release sustaining property and sustained plasma level. Besides, the preparation of Reference Example 15 which consists of only a solid solution shows insufficient adhesion and less sustaining of blood level because of too rapid release of the active ingredient, and the preparation of Reference Example 16 which does not contain a solid solution shows insufficient blood level because of slow dissolving out of the active ingredient. On the contrary, the preparation of the present invention shows excellent properties.

What is claimed is:

1. A sustained-release preparation applicable to mucous membrane in oral cavity, which comprises an active ingredient and a mixture of a polymer component (A) comprising one or more polymers selected from polyvinylpyrrolidone, polyvinyl alcohol, polyethylene glycol, alginic acid or a pharmaceutically acceptable salt thereof, and an alternating copolymer of maleic anhydride and methyl vinyl ether and a polymer component (B) comprising one or more polymers selected from polyacrylic acid and a pharmaceutically acceptable salt thereof, said polymer component (A) and polymer component (B) being contained in a ratio of 95:5 to 5:95 by weight.

2. The sustained-release preparation according to claim 1, wherein the active ingredient is nifedipine in the form of a solid solution in polyvinylpyrrolidone of the polymer component (A).

3. The sustained-release preparation according to claim 2, wherein the polyvinylpyrrolidone used for the solid solution has a molecular weight of $1 \times 10^4$ to $1 \times 10^5$.

4. A sustained-release preparation applicable to mucous membrane in oral cavity, which comprises
    a layer (I) comprising an active ingredient and one or more polymers selected from polyvinylpyrrolidone, polyvinyl alcohol, polyethylene glycol, alginic acid or a pharmaceutically acceptable salt thereof, and an alternating copolymer of maleic anhydride and methyl vinyl ether and optionally in admixture with conventional carrier and additives, said polymer being contained in an amount of not less than 20% by weight based on the whole weight of the layer (I), and a layer (II) comprising an active ingredient and a mixture of a polymer component (A) comprising one or more polymers selected from polyvinylpyrrolidone, polyvinyl alcohol, polyethylene glycol, alginic acid or a pharmaceutically acceptable salt thereof, and an alternating copolymer of maleic anhydride and methyl vinyl ether and a polymer component (B) comprising one or more polymers selected from polyacrylic acid and a pharmaceutically acceptable salt thereof, said polymer component (A) and polymer component (B) being contained in a ratio of 95:5 to 5:95 by weight.

5. The sustained-release preparation according to claim 4, wherein the layer (I) comprises a solid solution of nifedipine in polyvinylpyrrolidone and a pharmaceutically acceptable carrier, said polyvinylpyrrolidone being contained in an amount of 20 to 80% by weight based on the whole weight of the layer (I), and the layer (II) comprises a solid solution of nifedipine in polyvinylpyrrolidone and polyacrylic acid and/or a pharmaceutically acceptable salt thereof, said solid solution and polyacrylic acid and/or a salt thereof being contained in a ratio of 95:5 to 5:95 by weight.

6. The sustained-release preparation according to claim 5, wherein the polyvinylpyrrolidone used for the layer (I) has a molecular weight of $1 \times 10^4$ to $1 \times 10^5$, and the polyvinylpyrrolidone used for the layer (II) has a molecular weight of $1 \times 10^5$ to $4 \times 10^5$.

7. The sustained-release preparation of claim 1 wherein said active ingredient and said polymer components (A) and (B) are in admixture with at least one additive ingredient selected from the group consisting of excipients, lubricants, binding agents, and flavors and seasonings, said additive ingredients being incorporated in an amount of not more than 40% by weight based on the total weight of the preparation.

8. The sustained-release preparation of claim 7 wherein said at least one additive ingredient is selected from the group consisting of talc, stearic acid, salts of stearic acid, waxes, starches, dextrin, tragacanth, gelatin, hydroxypropyl cellulose, crystalline cellulose, lactose, mannitol, sorbitol, anhydrous calcium phosphate, citric acid, fumaric acid, tartaric acid, menthol and citrus fruit flavors.

* * * * *